(12) United States Patent

Meyer et al.

(10) Patent No.: US 12,558,133 B2
(45) Date of Patent: Feb. 24, 2026

(54) FLAT PLATE MECHANISMS FOR BONE LENGTHENING

(71) Applicant: Nuvasive Specialized Orthopedics, Inc., San Diego, CA (US)

(72) Inventors: Nathan Meyer, Vista, CA (US); Emmon Chen, Aliso Viejo, CA (US); Gabriel Buenviaje, Laguna Hills, CA (US); Kaila Lawson, Aliso Viejo, CA (US); Sherrie Yang, Aliso Viejo, CA (US)

(73) Assignee: NuVasive, Inc., San Diego, CA (US)

( * ) Notice: Subject to any disclaimer, the term of this patent is extended or adjusted under 35 U.S.C. 154(b) by 286 days.

(21) Appl. No.: 18/306,990

(22) Filed: Apr. 25, 2023

(65) Prior Publication Data

US 2024/0358418 A1 Oct. 31, 2024

(51) Int. Cl.
| | |
|---|---|
| *A61B 17/80* | (2006.01) |
| *A61B 17/68* | (2006.01) |
| A61B 17/00 | (2006.01) |
| A61F 2/30 | (2006.01) |

(52) U.S. Cl.
CPC ...... *A61B 17/8009* (2013.01); *A61B 17/8004* (2013.01); *A61B 17/8023* (2013.01); *A61B 2017/00407* (2013.01); *A61B 2017/681* (2013.01); *A61F 2002/30706* (2013.01)

(58) Field of Classification Search
CPC ............ A61B 17/8004; A61B 17/8009; A61B 17/8023; A61B 17/60; A61B 17/66; A61B 17/663; A61B 17/6416; A61B 17/6425; A61B 17/6433; A61B 17/6441;
(Continued)

(56) References Cited

U.S. PATENT DOCUMENTS

| | | | |
|---|---|---|---|
| 2,702,031 | A | 2/1955 | Leslie |
| 2,726,726 | A | 12/1955 | Le et al. |
| 3,111,945 | A | 11/1963 | Von Solbrig |

(Continued)

FOREIGN PATENT DOCUMENTS

| | | |
|---|---|---|
| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Matthew J Lawson

(57) ABSTRACT

Provided herein is an adjustable implant configured to non-invasively guide bone growth in a patient. The adjustable implant includes a first portion configured to couple to a first bone segment and a second portion at least partially disposed within the first portion and configured to couple to a second bone segment. The adjustable implant includes a drive assembly configured to be transcutaneously actuated, and to drive rotation of a gear assembly configured to rotate about a first axis, and drive axial translation of the second portion along a second axis. Non-invasive actuation of the drive assembly therefore causes the adjustable implant to distract or retract along the second axis.

16 Claims, 15 Drawing Sheets

(58) Field of Classification Search

CPC .............. A61B 17/645; A61B 17/6458; A61B 17/6466; A61B 17/6475

See application file for complete search history.

(56) References Cited

U.S. PATENT DOCUMENTS

| | | | |
|---|---|---|---|
| 3,372,476 A | 3/1968 | Richard | |
| 3,377,576 A | 4/1968 | Edwin | |
| 3,512,901 A | 5/1970 | Law | |
| 3,597,781 A | 8/1971 | Eibes | |
| 3,900,025 A | 8/1975 | Barnes, Jr. | |
| 3,915,151 A | 10/1975 | Kraus | |
| RE28,907 E | 7/1976 | Eibes et al. | |
| 3,976,060 A | 8/1976 | Hildebrandt et al. | |
| 4,010,758 A | 3/1977 | Rockland et al. | |
| 4,056,743 A | 11/1977 | Clifford et al. | |
| 4,068,821 A | 1/1978 | Morrison | |
| 4,078,559 A | 3/1978 | Nissinen | |
| 4,204,541 A | 5/1980 | Kapitanov | |
| 4,357,946 A | 11/1982 | Dutcher et al. | |
| 4,386,603 A | 6/1983 | Mayfield | |
| 4,448,191 A | 5/1984 | Rodnyansky et al. | |
| 4,486,176 A | 12/1984 | Tardieu et al. | |
| 4,501,266 A | 2/1985 | McDaniel | |
| 4,522,501 A | 6/1985 | Shannon | |
| 4,537,520 A | 8/1985 | Ochiai et al. | |
| 4,550,279 A | 10/1985 | Klein | |
| 4,561,798 A | 12/1985 | Elcrin et al. | |
| 4,573,454 A | 3/1986 | Hoffman | |
| 4,592,355 A | 6/1986 | Antebi | |
| 4,595,007 A | 6/1986 | Mericle | |
| 4,642,257 A | 2/1987 | Chase | |
| 4,658,809 A | 4/1987 | Ulrich et al. | |
| 4,700,091 A | 10/1987 | Wuthrich | |
| 4,747,832 A | 5/1988 | Buffet | |
| 4,854,304 A | 8/1989 | Zielke | |
| 4,904,861 A | 2/1990 | Epstein et al. | |
| 4,931,055 A | 6/1990 | Bumpus et al. | |
| 4,940,467 A | 7/1990 | Tronzo | |
| 4,957,495 A | 9/1990 | Kluger | |
| 4,973,331 A | 11/1990 | Pursley et al. | |
| 5,010,879 A | 4/1991 | Moriya et al. | |
| 5,030,235 A | 7/1991 | Campbell, Jr. | |
| 5,041,112 A | 8/1991 | Mingozzi et al. | |
| 5,064,004 A | 11/1991 | Lundell | |
| 5,074,882 A | 12/1991 | Grammont et al. | |
| 5,092,889 A | 3/1992 | Campbell, Jr. | |
| 5,133,716 A | 7/1992 | Plaza | |
| 5,142,407 A | 8/1992 | Varaprasad et al. | |
| 5,156,605 A | 10/1992 | Pursley et al. | |
| 5,263,955 A | 11/1993 | Baumgart et al. | |
| 5,290,289 A | 3/1994 | Sanders et al. | |
| 5,306,275 A | 4/1994 | Bryan | |
| 5,330,503 A | 7/1994 | Yoon | |
| 5,334,202 A | 8/1994 | Carter | |
| 5,336,223 A | 8/1994 | Rogers | |
| 5,356,411 A | 10/1994 | Spievack | |
| 5,356,424 A | 10/1994 | Buzerak et al. | |
| 5,364,396 A | 11/1994 | Robinson et al. | |
| 5,403,322 A | 4/1995 | Herzenberg et al. | |
| 5,429,638 A | 7/1995 | Muschler et al. | |
| 5,437,266 A | 8/1995 | McPherson et al. | |
| 5,466,261 A | 11/1995 | Richelsoph | |
| 5,468,030 A | 11/1995 | Walling | |
| 5,480,437 A | 1/1996 | Draenert | |
| 5,509,888 A | 4/1996 | Miller | |
| 5,516,335 A | 5/1996 | Kummer et al. | |
| 5,527,309 A | 6/1996 | Shelton | |
| 5,536,269 A | 7/1996 | Spievack | |
| 5,549,610 A | 8/1996 | Russell et al. | |
| 5,573,012 A | 11/1996 | McEwan | |
| 5,575,790 A | 11/1996 | Chen et al. | |
| 5,582,616 A | 12/1996 | Bolduc et al. | |
| 5,620,445 A | 4/1997 | Brosnahan et al. | |
| 5,620,449 A | 4/1997 | Faccioli et al. | |
| 5,626,579 A | 5/1997 | Muschler et al. | |
| 5,626,613 A | 5/1997 | Schmieding | |
| 5,632,744 A | 5/1997 | Campbell, Jr. | |
| 5,659,217 A | 8/1997 | Petersen | |
| 5,662,683 A | 9/1997 | Kay | |
| 5,672,175 A | 9/1997 | Martin | |
| 5,672,177 A | 9/1997 | Seldin | |
| 5,700,263 A | 12/1997 | Schendel | |
| 5,704,938 A | 1/1998 | Staehlin et al. | |
| 5,704,939 A | 1/1998 | Justin | |
| 5,720,746 A | 2/1998 | Soubeiran | |
| 5,743,910 A | 4/1998 | Bays et al. | |
| 5,762,599 A | 6/1998 | Sohn | |
| 5,771,903 A | 6/1998 | Jakobsson | |
| 5,810,815 A | 9/1998 | Morales | |
| 5,827,286 A | 10/1998 | Incavo et al. | |
| 5,830,221 A | 11/1998 | Stein et al. | |
| 5,879,375 A | 3/1999 | Larson, Jr. et al. | |
| 5,902,304 A | 5/1999 | Walker et al. | |
| 5,935,127 A | 8/1999 | Border | |
| 5,945,762 A | 8/1999 | Chen et al. | |
| 5,961,553 A | 10/1999 | Coty et al. | |
| 5,976,138 A | 11/1999 | Baumgart et al. | |
| 5,979,456 A | 11/1999 | Magovern | |
| 6,022,349 A | 2/2000 | McLeod et al. | |
| 6,033,412 A * | 3/2000 | Losken .............. A61B 17/7216 606/57 |
| 6,034,296 A | 3/2000 | Elvin et al. | |
| 6,102,922 A | 8/2000 | Jakobsson et al. | |
| 6,106,525 A | 8/2000 | Sachse | |
| 6,113,599 A * | 9/2000 | Landsberger ........ A61B 17/663 606/57 |
| 6,126,660 A | 10/2000 | Dietz | |
| 6,126,661 A | 10/2000 | Faccioli et al. | |
| 6,138,681 A | 10/2000 | Chen et al. | |
| 6,139,316 A | 10/2000 | Sachdeva et al. | |
| 6,162,223 A | 12/2000 | Orsak et al. | |
| 6,183,476 B1 | 2/2001 | Gerhardt et al. | |
| 6,200,317 B1 | 3/2001 | Aalsma et al. | |
| 6,234,956 B1 | 5/2001 | He et al. | |
| 6,241,730 B1 | 6/2001 | Alby | |
| 6,245,075 B1 | 6/2001 | Betz et al. | |
| 6,315,784 B1 | 11/2001 | Djurovic | |
| 6,319,255 B1 | 11/2001 | Grundei et al. | |
| 6,331,744 B1 | 12/2001 | Chen et al. | |
| 6,336,929 B1 | 1/2002 | Justin | |
| 6,343,568 B1 | 2/2002 | McClasky | |
| 6,358,283 B1 | 3/2002 | Hogfors et al. | |
| 6,375,682 B1 | 4/2002 | Fleischmann et al. | |
| 6,389,187 B1 | 5/2002 | Greenaway et al. | |
| 6,400,980 B1 | 6/2002 | Lemelson | |
| 6,402,753 B1 | 6/2002 | Cole et al. | |
| 6,409,175 B1 | 6/2002 | Evans et al. | |
| 6,416,516 B1 | 7/2002 | Stauch et al. | |
| 6,499,907 B1 | 12/2002 | Baur | |
| 6,500,110 B1 | 12/2002 | Davey et al. | |
| 6,508,820 B2 | 1/2003 | Bales | |
| 6,510,345 B1 | 1/2003 | Van Bentem | |
| 6,537,196 B1 | 3/2003 | Creighton, IV et al. | |
| 6,554,831 B1 | 4/2003 | Rivard et al. | |
| 6,565,573 B1 | 5/2003 | Ferrante et al. | |
| 6,565,576 B1 | 5/2003 | Stauch et al. | |
| 6,582,313 B2 | 6/2003 | Perrow | |
| 6,583,630 B2 | 6/2003 | Mendes et al. | |
| 6,616,669 B2 | 9/2003 | Ogilvie et al. | |
| 6,626,917 B1 | 9/2003 | Craig | |
| 6,656,135 B2 | 12/2003 | Zogbi et al. | |
| 6,656,194 B1 | 12/2003 | Gannoe et al. | |
| 6,667,725 B1 | 12/2003 | Simons et al. | |
| 6,673,079 B1 | 1/2004 | Kane | |
| 6,702,816 B2 | 3/2004 | Buhler | |
| 6,706,042 B2 | 3/2004 | Taylor | |
| 6,709,293 B2 | 3/2004 | Mori et al. | |
| 6,730,087 B1 | 5/2004 | Butsch | |
| 6,761,503 B2 | 7/2004 | Breese | |
| 6,769,499 B2 | 8/2004 | Cargill et al. | |
| 6,789,442 B2 | 9/2004 | Forch | |
| 6,796,984 B2 | 9/2004 | Soubeiran | |
| 6,802,844 B2 | 10/2004 | Ferree | |

(56)                    References Cited

U.S. PATENT DOCUMENTS

| | | | |
|---|---|---|---|
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,617,220 B2 | 12/2013 | Skaggs |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |

(56) References Cited

U.S. PATENT DOCUMENTS

| | | | |
|---|---|---|---|
| 8,636,771 | B2 | 1/2014 | Butler et al. |
| 8,636,802 | B2 | 1/2014 | Serhan et al. |
| 8,641,719 | B2 | 2/2014 | Gephart et al. |
| 8,641,723 | B2 | 2/2014 | Connor |
| 8,657,856 | B2 | 2/2014 | Gephart et al. |
| 8,663,285 | B2 | 3/2014 | Dall et al. |
| 8,663,287 | B2 | 3/2014 | Butler et al. |
| 8,668,719 | B2 | 3/2014 | Alamin et al. |
| 8,709,090 | B2 | 4/2014 | Makower et al. |
| 8,758,347 | B2 | 6/2014 | Weiner et al. |
| 8,758,355 | B2 | 6/2014 | Fisher et al. |
| 8,771,272 | B2 | 7/2014 | LeCronier et al. |
| 8,777,947 | B2 | 7/2014 | Zahrly et al. |
| 8,777,995 | B2 | 7/2014 | McClintock et al. |
| 8,790,343 | B2 | 7/2014 | McClellan et al. |
| 8,790,409 | B2 | 7/2014 | Van Den Heuvel et al. |
| 8,828,058 | B2 | 9/2014 | Elsebaie et al. |
| 8,828,087 | B2 | 9/2014 | Stone et al. |
| 8,840,651 | B2 | 9/2014 | Reiley |
| 8,870,881 | B2 | 10/2014 | Rezach et al. |
| 8,870,959 | B2 | 10/2014 | Arnin |
| 8,915,915 | B2 | 12/2014 | Harrison et al. |
| 8,915,917 | B2 | 12/2014 | Doherty et al. |
| 8,920,422 | B2 | 12/2014 | Homeier et al. |
| 8,945,188 | B2 | 2/2015 | Rezach et al. |
| 8,961,521 | B2 | 2/2015 | Keefer et al. |
| 8,961,567 | B2 * | 2/2015 | Hunziker ........... A61B 17/7016 |
| | | | 606/259 |
| 8,968,402 | B2 | 3/2015 | Myers et al. |
| 8,992,527 | B2 | 3/2015 | Guichet |
| 9,022,917 | B2 | 5/2015 | Kasic et al. |
| 9,044,218 | B2 | 6/2015 | Young |
| 9,060,810 | B2 | 6/2015 | Kercher et al. |
| 9,078,703 | B2 | 7/2015 | Arnin |
| 9,179,938 | B2 | 11/2015 | Pool et al. |
| 11,974,768 | B2 * | 5/2024 | Bono ............. A61B 17/320758 |
| 12,076,041 | B2 * | 9/2024 | Akilian ............ A61B 17/32002 |
| 12,239,326 | B2 * | 3/2025 | Bozung ................. A61B 34/20 |
| 12,262,908 | B2 * | 4/2025 | Collinson ............. A61B 17/42 |
| 2002/0050112 | A1 | 5/2002 | Koch et al. |
| 2002/0072758 | A1 | 6/2002 | Reo et al. |
| 2002/0164905 | A1 | 11/2002 | Bryant |
| 2003/0040671 | A1 | 2/2003 | Somogyi et al. |
| 2003/0144669 | A1 | 7/2003 | Robinson |
| 2003/0220643 | A1 | 11/2003 | Ferree |
| 2003/0220644 | A1 | 11/2003 | Thelen et al. |
| 2004/0011137 | A1 | 1/2004 | Hnat et al. |
| 2004/0011365 | A1 | 1/2004 | Govari et al. |
| 2004/0019353 | A1 | 1/2004 | Freid et al. |
| 2004/0023623 | A1 | 2/2004 | Stauch et al. |
| 2004/0055610 | A1 | 3/2004 | Forsell |
| 2004/0133219 | A1 | 7/2004 | Forsell |
| 2004/0138725 | A1 | 7/2004 | Forsell |
| 2004/0193266 | A1 | 9/2004 | Meyer |
| 2005/0034705 | A1 | 2/2005 | McClendon |
| 2005/0049617 | A1 | 3/2005 | Chatlynne et al. |
| 2005/0065529 | A1 | 3/2005 | Liu et al. |
| 2005/0090823 | A1 | 4/2005 | Bartimus |
| 2005/0159754 | A1 | 7/2005 | Odrich |
| 2005/0234448 | A1 | 10/2005 | McCarthy |
| 2005/0234462 | A1 | 10/2005 | Hershberger |
| 2005/0246034 | A1 | 11/2005 | Soubeiran |
| 2005/0261779 | A1 | 11/2005 | Meyer |
| 2005/0272976 | A1 | 12/2005 | Tanaka et al. |
| 2006/0004459 | A1 | 1/2006 | Hazebrouck et al. |
| 2006/0009767 | A1 | 1/2006 | Kiester |
| 2006/0036259 | A1 | 2/2006 | Carl et al. |
| 2006/0036323 | A1 | 2/2006 | Carl et al. |
| 2006/0036324 | A1 | 2/2006 | Sachs et al. |
| 2006/0047282 | A1 | 3/2006 | Gordon |
| 2006/0058792 | A1 | 3/2006 | Hynes |
| 2006/0069447 | A1 | 3/2006 | DiSilvestro et al. |
| 2006/0074448 | A1 | 4/2006 | Harrison et al. |
| 2006/0079897 | A1 | 4/2006 | Harrison et al. |
| 2006/0136062 | A1 | 6/2006 | DiNello et al. |
| 2006/0142767 | A1 | 6/2006 | Green et al. |
| 2006/0155279 | A1 | 7/2006 | Ogilvie |
| 2006/0195087 | A1 | 8/2006 | Sacher et al. |
| 2006/0195088 | A1 | 8/2006 | Sacher et al. |
| 2006/0200134 | A1 | 9/2006 | Freid et al. |
| 2006/0204156 | A1 | 9/2006 | Takehara et al. |
| 2006/0235299 | A1 | 10/2006 | Martinelli |
| 2006/0235424 | A1 | 10/2006 | Vitale et al. |
| 2006/0241746 | A1 | 10/2006 | Shaoulian et al. |
| 2006/0241767 | A1 | 10/2006 | Doty |
| 2006/0249914 | A1 | 11/2006 | Dulin |
| 2006/0271107 | A1 | 11/2006 | Harrison et al. |
| 2006/0282073 | A1 | 12/2006 | Simanovsky |
| 2006/0293683 | A1 | 12/2006 | Stauch |
| 2007/0010814 | A1 | 1/2007 | Stauch |
| 2007/0010887 | A1 | 1/2007 | Williams et al. |
| 2007/0021644 | A1 | 1/2007 | Woolson et al. |
| 2007/0031131 | A1 | 2/2007 | Griffitts |
| 2007/0043376 | A1 | 2/2007 | Leatherbury et al. |
| 2007/0050030 | A1 | 3/2007 | Kim |
| 2007/0118215 | A1 | 5/2007 | Moaddeb |
| 2007/0161984 | A1 | 7/2007 | Cresina et al. |
| 2007/0173837 | A1 | 7/2007 | Chan et al. |
| 2007/0179493 | A1 | 8/2007 | Kim |
| 2007/0185374 | A1 | 8/2007 | Kick et al. |
| 2007/0233098 | A1 | 10/2007 | Mastrorio et al. |
| 2007/0239159 | A1 | 10/2007 | Altarac et al. |
| 2007/0239161 | A1 | 10/2007 | Giger et al. |
| 2007/0255088 | A1 | 11/2007 | Jacobson et al. |
| 2007/0270803 | A1 | 11/2007 | Giger et al. |
| 2007/0276368 | A1 | 11/2007 | Trieu et al. |
| 2007/0276369 | A1 | 11/2007 | Allard et al. |
| 2007/0276373 | A1 | 11/2007 | Malandain |
| 2007/0276378 | A1 | 11/2007 | Harrison et al. |
| 2007/0276493 | A1 | 11/2007 | Malandain et al. |
| 2007/0288024 | A1 | 12/2007 | Gollogly |
| 2007/0288183 | A1 | 12/2007 | Bulkes et al. |
| 2008/0009792 | A1 | 1/2008 | Henniges et al. |
| 2008/0015577 | A1 | 1/2008 | Loeb |
| 2008/0021454 | A1 | 1/2008 | Chao et al. |
| 2008/0021455 | A1 | 1/2008 | Chao et al. |
| 2008/0021456 | A1 | 1/2008 | Gupta et al. |
| 2008/0027436 | A1 | 1/2008 | Cournoyer et al. |
| 2008/0033431 | A1 | 2/2008 | Jung et al. |
| 2008/0033436 | A1 | 2/2008 | Song et al. |
| 2008/0051784 | A1 | 2/2008 | Gollogly |
| 2008/0082118 | A1 | 4/2008 | Edidin et al. |
| 2008/0086128 | A1 | 4/2008 | Lewis |
| 2008/0097487 | A1 | 4/2008 | Pool et al. |
| 2008/0097496 | A1 | 4/2008 | Chang et al. |
| 2008/0108995 | A1 | 5/2008 | Conway et al. |
| 2008/0161933 | A1 | 7/2008 | Grotz et al. |
| 2008/0167685 | A1 | 7/2008 | Allard et al. |
| 2008/0172063 | A1 | 7/2008 | Taylor |
| 2008/0177319 | A1 | 7/2008 | Schwab |
| 2008/0177326 | A1 | 7/2008 | Thompson |
| 2008/0190237 | A1 | 8/2008 | Radinger et al. |
| 2008/0228186 | A1 | 9/2008 | Gall et al. |
| 2008/0255615 | A1 | 10/2008 | Vittur et al. |
| 2008/0272928 | A1 | 11/2008 | Shuster |
| 2008/0275557 | A1 | 11/2008 | Makower et al. |
| 2009/0030462 | A1 | 1/2009 | Buttermann |
| 2009/0076597 | A1 | 3/2009 | Dahlgren et al. |
| 2009/0082815 | A1 | 3/2009 | Zylber et al. |
| 2009/0088803 | A1 | 4/2009 | Justis et al. |
| 2009/0093820 | A1 | 4/2009 | Trieu et al. |
| 2009/0093890 | A1 | 4/2009 | Gelbart |
| 2009/0112263 | A1 * | 4/2009 | Pool ..................... A61B 17/707 |
| | | | 600/587 |
| 2009/0163780 | A1 | 6/2009 | Tieu |
| 2009/0171356 | A1 | 7/2009 | Klett |
| 2009/0192514 | A1 * | 7/2009 | Feinberg ............ A61B 17/8004 |
| | | | 606/90 |
| 2009/0198144 | A1 | 8/2009 | Phillips et al. |
| 2009/0216113 | A1 | 8/2009 | Meier et al. |
| 2009/0275984 | A1 | 11/2009 | Kim et al. |
| 2010/0004654 | A1 | 1/2010 | Schmitz et al. |
| 2010/0049204 | A1 | 2/2010 | Soubeiran |
| 2010/0057127 | A1 | 3/2010 | McGuire et al. |

(56) References Cited

U.S. PATENT DOCUMENTS

| | | | |
|---|---|---|---|
| 2010/0094306 A1* | 4/2010 | Chang | A61B 17/7023 |
| | | | 606/90 |
| 2010/0100185 A1 | 4/2010 | Trieu et al. | |
| 2010/0106192 A1 | 4/2010 | Barry | |
| 2010/0114322 A1 | 5/2010 | Clifford et al. | |
| 2010/0130941 A1 | 5/2010 | Conlon et al. | |
| 2010/0137872 A1 | 6/2010 | Kam et al. | |
| 2010/0145449 A1 | 6/2010 | Makower et al. | |
| 2010/0145462 A1 | 6/2010 | Ainsworth et al. | |
| 2010/0168751 A1 | 7/2010 | Anderson et al. | |
| 2010/0249782 A1 | 9/2010 | Durham | |
| 2010/0256626 A1 | 10/2010 | Muller et al. | |
| 2010/0262239 A1 | 10/2010 | Boyden et al. | |
| 2010/0318129 A1 | 12/2010 | Seme et al. | |
| 2010/0331883 A1 | 12/2010 | Schmitz et al. | |
| 2011/0004076 A1 | 1/2011 | Janna et al. | |
| 2011/0057756 A1 | 3/2011 | Marinescu et al. | |
| 2011/0066188 A1 | 3/2011 | Seme et al. | |
| 2011/0098748 A1 | 4/2011 | Jangra | |
| 2011/0152725 A1 | 6/2011 | Demir et al. | |
| 2011/0196435 A1 | 8/2011 | Forsell | |
| 2011/0202138 A1 | 8/2011 | Shenoy et al. | |
| 2011/0238126 A1 | 9/2011 | Soubeiran | |
| 2011/0257655 A1 | 10/2011 | Copf, Jr. | |
| 2011/0284014 A1 | 11/2011 | Cadeddu et al. | |
| 2012/0019341 A1 | 1/2012 | Gabay et al. | |
| 2012/0019342 A1 | 1/2012 | Gabay et al. | |
| 2012/0053633 A1 | 3/2012 | Stauch | |
| 2012/0088953 A1 | 4/2012 | King | |
| 2012/0109207 A1 | 5/2012 | Trieu | |
| 2012/0116535 A1 | 5/2012 | Ratron et al. | |
| 2012/0158061 A1 | 6/2012 | Koch et al. | |
| 2012/0172883 A1 | 7/2012 | Sayago | |
| 2012/0179215 A1 | 7/2012 | Soubeiran | |
| 2012/0221106 A1 | 8/2012 | Makower et al. | |
| 2012/0271353 A1 | 10/2012 | Barry | |
| 2012/0296234 A1 | 11/2012 | Wilhelm et al. | |
| 2012/0329882 A1 | 12/2012 | Messersmith et al. | |
| 2013/0013066 A1 | 1/2013 | Landry et al. | |
| 2013/0072932 A1 | 3/2013 | Stauch | |
| 2013/0123847 A1 | 5/2013 | Anderson et al. | |
| 2013/0138017 A1 | 5/2013 | Jundt et al. | |
| 2013/0138154 A1 | 5/2013 | Reiley | |
| 2013/0150863 A1 | 6/2013 | Baumgartner | |
| 2013/0150889 A1 | 6/2013 | Fening et al. | |
| 2013/0178903 A1 | 7/2013 | Abdou | |
| 2013/0211521 A1 | 8/2013 | Shenoy et al. | |
| 2013/0245692 A1 | 9/2013 | Hayes et al. | |
| 2013/0253344 A1 | 9/2013 | Griswold et al. | |
| 2013/0253587 A1 | 9/2013 | Carls et al. | |
| 2013/0261672 A1 | 10/2013 | Horvath | |
| 2013/0296863 A1 | 11/2013 | Globerman et al. | |
| 2013/0296864 A1 | 11/2013 | Burley et al. | |
| 2013/0296940 A1 | 11/2013 | Northcutt et al. | |
| 2013/0325006 A1 | 12/2013 | Michelinie et al. | |
| 2013/0325071 A1 | 12/2013 | Niemiec et al. | |
| 2014/0005788 A1 | 1/2014 | Haaja et al. | |
| 2014/0025172 A1 | 1/2014 | Lucas et al. | |
| 2014/0052134 A1 | 2/2014 | Orisek | |
| 2014/0058392 A1 | 2/2014 | Mueckter et al. | |
| 2014/0058450 A1 | 2/2014 | Arlet | |
| 2014/0066987 A1 | 3/2014 | Hestad et al. | |
| 2014/0088715 A1 | 3/2014 | Ciupik | |
| 2014/0128920 A1 | 5/2014 | Kantelhardt | |
| 2014/0155946 A1 | 6/2014 | Skinlo et al. | |
| 2014/0163664 A1 | 6/2014 | Goldsmith | |
| 2014/0236234 A1 | 8/2014 | Kroll et al. | |
| 2014/0236311 A1 | 8/2014 | Vicatos et al. | |
| 2014/0257412 A1 | 9/2014 | Patty et al. | |
| 2014/0277446 A1 | 9/2014 | Clifford et al. | |
| 2014/0296918 A1 | 10/2014 | Fening et al. | |
| 2014/0303538 A1 | 10/2014 | Baym et al. | |
| 2014/0303539 A1 | 10/2014 | Baym et al. | |
| 2014/0358150 A1 | 12/2014 | Kaufman et al. | |
| 2015/0105782 A1 | 4/2015 | D'Lima et al. | |
| 2015/0105824 A1 | 4/2015 | Moskowitz et al. | |
| 2015/0272644 A1 | 10/2015 | Noon et al. | |
| 2021/0386464 A1 | 12/2021 | Gaudreau et al. | |
| 2022/0015751 A1* | 1/2022 | Chevalier | A61B 17/7216 |
| 2022/0031375 A1 | 2/2022 | Walker et al. | |
| 2022/0125493 A1* | 4/2022 | Taylor | A61B 17/8019 |
| 2022/0346839 A1* | 11/2022 | El Amm | A61B 17/66 |
| 2022/0387086 A1* | 12/2022 | Penn, IV | A61B 17/8071 |
| 2023/0210566 A1* | 7/2023 | Ishihara | A61B 90/98 |
| | | | 606/282 |
| 2023/0285045 A1* | 9/2023 | Truckai | A61B 1/015 |
| 2024/0130765 A1* | 4/2024 | Lopez Camacho | |
| | | | A61B 17/8004 |
| 2024/0156482 A1* | 5/2024 | Barnes | A61B 17/1659 |
| 2024/0358412 A1* | 10/2024 | Camacho | A61B 17/7059 |

FOREIGN PATENT DOCUMENTS

| | | | |
|---|---|---|---|
| DE | 1541262 A1 | 6/1969 | |
| DE | 8515687 U1 | 12/1985 | |
| DE | 19626230 A1 | 1/1998 | |
| DE | 19745654 A1 | 4/1999 | |
| DE | 102005045070 A1 | 4/2007 | |
| EP | 0663184 A1 | 7/1995 | |
| EP | 1905388 A1 | 4/2008 | |
| FR | 2901991 A1 | 12/2007 | |
| FR | 2900563 B1 | 8/2008 | |
| FR | 2892617 B1 | 9/2008 | |
| FR | 2916622 B1 | 9/2009 | |
| FR | 2961386 B1 | 12/2011 | |
| JP | 1975159186 A | 12/1975 | |
| JP | H0956736 | 3/1997 | |
| JP | 2002500063 A | 1/2002 | |
| JP | 2009542272 A | 12/2009 | |
| WO | WO1998044858 A1 | 10/1998 | |
| WO | WO1999051160 A1 | 10/1999 | |
| WO | WO2001024697 A1 | 4/2001 | |
| WO | WO2001045485 A3 | 6/2001 | |
| WO | WO2001045487 A2 | 6/2001 | |
| WO | WO2001067973 A2 | 9/2001 | |
| WO | WO2001078614 A1 | 10/2001 | |
| WO | WO2007013059 A3 | 2/2007 | |
| WO | WO2007015239 A3 | 2/2007 | |
| WO | WO2011116158 A3 | 9/2011 | |
| WO | WO2013119528 A1 | 8/2013 | |
| WO | WO2014040013 A1 | 3/2014 | |
| WO | 2016105524 A1 | 6/2016 | |
| WO | 2022015898 A1 | 1/2022 | |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid PortTM System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

(56)              References Cited

OTHER PUBLICATIONS

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening. ", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents. ", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

Micromotion, "Micro Drive Engineering. General catalogue.", 2009, pp. 14-24.

(56) References Cited

OTHER PUBLICATIONS

Mineiro et al., "Subcutaneous rodding for progressive spinal curvatures: Early results.", Journal of Pediatric Orthopaedics, 2002, pp. 290-295, 22, No. 3.

Moe et al., "Harrington instrumentation without fusion plus external orthotic support for the treatment of difficult curvature problems in young children.", Clinical Orthopaedics and Related Research, 1984, pp. 35-45, 185.

Montague et al., "Magnetic gear dynamics for servo control.", Melecon 2010 - 2010 15th IEEE Mediterranean Electrotechnical Conference, Valletta, 2010, pp. 1192-1197.

Montague et al., "Servo control of magnetic gears.", IEEE/ASME Transactions on Mechatronics, 2012, pp. 269-278, 17, No. 2.

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work?. ", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted noninvasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "Veptr Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results. ", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

* cited by examiner

1500

Implanting an adjustable implant to a first bone segment and a second bone segment, 1510

Actuating a drive assembly about a first axis, 1520

Distracting the second bone segment relative to the first bone segment along a second axis, 1530

Permitting continued bone growth, 1540

FLAT PLATE MECHANISMS FOR BONE LENGTHENING

TECHNICAL FIELD

The subject matter described herein relates to an adjustable implant, distraction and compression system, and related methods.

BACKGROUND

Distraction osteogenesis procedures cause two bone segments to distract apart, allowing new bone tissue to form between the two bone segments. Distraction osteogenesis procedures may be useful, for example, to increase the length of a bone (e.g., femur, tibia, etc.) at a pre-determined rate, such as one millimeter per day, thereby allowing new bone tissue to form in a gap between the segments. One limitation of devices, systems, and methods known in the art of distraction osteogenesis procedures is the size and/or shape of known devices which limit the implantation site and/or distraction osteogenesis procedures that can be performed. Embodiments of the present disclosure aim to address these challenges, as well as other challenges generally with distraction osteogenesis devices, systems, and associated methods.

SUMMARY

All aspects, examples and features mentioned below can be combined in any technically possible way.

An aspect of the disclosure provides an adjustable implant including: a first portion configured to couple to a first bone segment; a drive assembly disposed within the first portion and configured to drive rotational motion about a first axis; a second portion configured to couple to a second bone segment and axially translate relative to the first portion along a second axis; and a lead screw disposed at least partially within the first and second portions along the second axis. The lead screw is rotatably coupled to the drive assembly such that rotational motion about the first axis drives rotational motion of the lead screw about the second axis, thereby causing the second portion to axially translate along the second axis relative to the first portion.

Another aspect of the disclosure provides an adjustable implant including: a first portion configured to couple to a first bone segment; a gear assembly disposed in the first portion; a drive assembly configured to rotatably engage the gear assembly and to rotate about a first axis, wherein the drive assembly is configured to drive rotational motion of the gear assembly about a second axis; a lead screw disposed at least partially within the first portion, and extending along a third axis; and a second portion configured to couple to a second bone segment. The lead screw is at least partially disposed within the second portion and rotatably coupled to the drive assembly, such that rotational motion of the drive assembly about the first axis drives rotational motion of the gear assembly about the second axis, which drives rotational motion of the lead screw about the third axis, thereby causing the second portion to axially translate along the third axis relative to the first portion.

Another aspect of the disclosure provides an adjustable implant including: a first portion configured to couple to a first bone segment; and a drive assembly disposed within the first portion and configured to rotate about a first axis. The drive assembly includes a driver configured to rotate about the first axis, and a drive shaft rotatably coupled to the driver. The adjustable implant further includes a second portion configured to couple to a second bone segment and axially translate relative to the first portion along a second axis; and a ratchet assembly disposed at least partially within the first and second portions. The ratchet assembly is configured to actuate axial translation relative to the first portion along the second axis in response to rotation of the drive assembly about the first axis, and to inhibit retraction of the second portion relative to the first portion along the second axis.

Two or more aspects described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
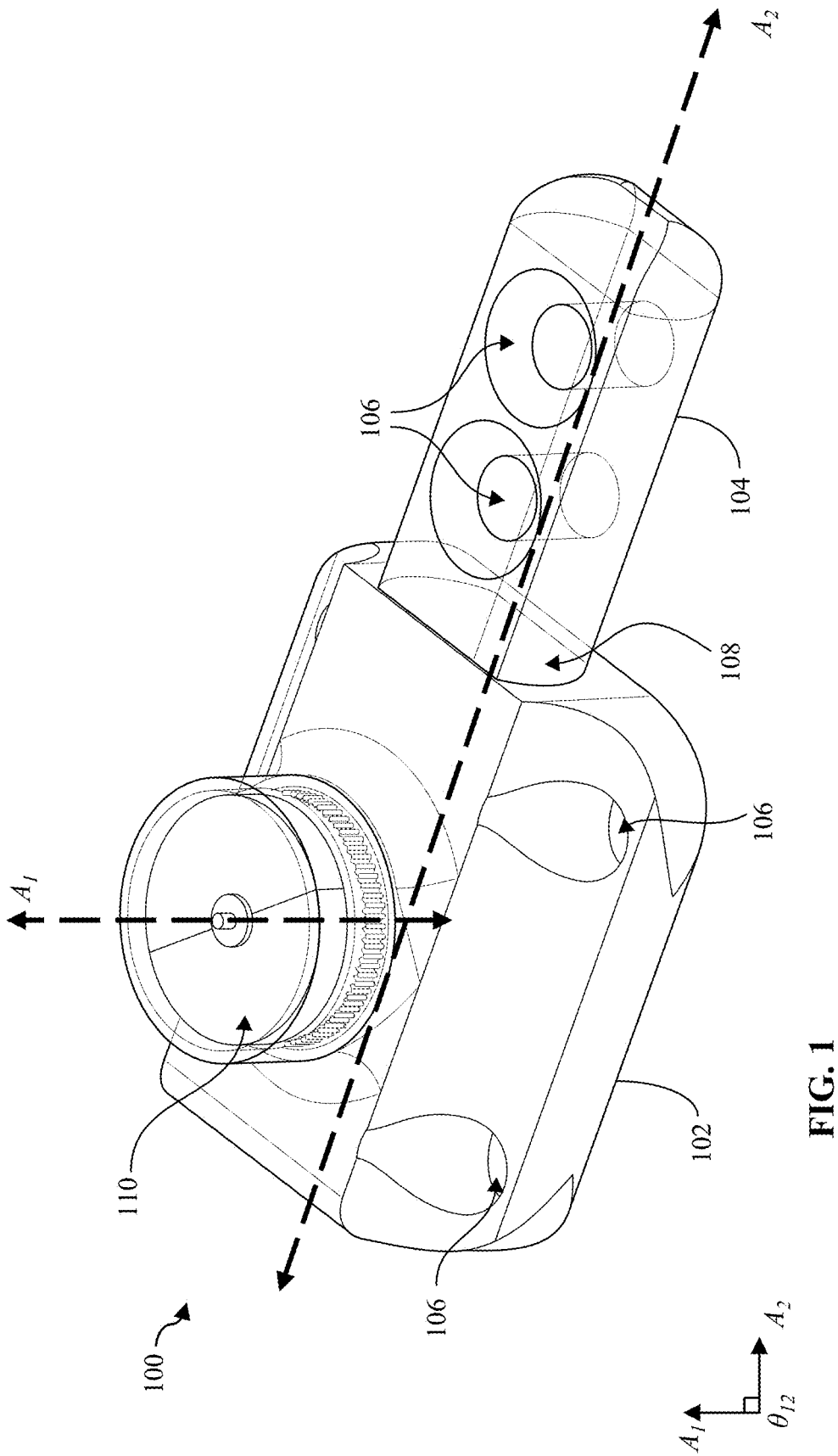
FIG. 1 illustrates an assembled perspective view of one embodiment of an adjustable implant according to the present disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of adjustable implants, distraction and compression systems, and related methods. Such embodiments include, for example, an adjustable implant having a first portion configured to couple to a first bone segment and a second portion configured to couple to a second bone segment of a patient. The second portion may be at least partially disposed within the first portion and configured to axially translate along an axis relative to the first portion. The first and second portions of the adjustable implant may include one or more apertures configured to receive, for example, a fixation anchor therein to couple the first and second portions of the adjustable implant to the first and second bone segments, respectively. The adjustable implant may include a drive assembly configured to drive rotational movement of a lead screw to move the second portion relative to the first portion, thereby adjusting the distance between the first and second bone segments for performing distraction osteogenesis. The adjustable implant may be configured to be externally controlled by an external adjustment device and may therefore be non-invasively adjustable in such embodiments.

As shown in FIG. 1, adjustable implant 100 includes a first portion 102 and a second portion 104 at least partially disposed within the first portion 102. For example, the first portion 102 may be a housing, and the second portion 104 may be a movable rod disposed at least partially within the housing. The illustrated first and second portions 102, 104 each include a flat plate shaped and dimensioned to engage a bone segment of a patient. The first portion 102 is configured to be fixed to the bone at a first location (e.g., a first bone segment) and the second portion 104 is configured to be fixed to the bone at a second location (e.g., a second bone segment). The first and second portions 102, 104 may each include one or more fixation apertures 106 configured to receive one or more fixation screws therein. The fixation screw(s) may be configured to couple the first and second portions 102, 104 to the bone at the first and second locations, respectively. In some embodiments, the one or more fixation apertures 106 include a locking screw hole having internal threads for threadingly engaging a thread on a head of a fixation screw, as will be described herein. One or both of the first and second portions 102, 104 can be configured for extramedullary attachment to bone.

In order to grow or lengthen bone, the bone can have a pre-existing separation or is purposely cut or broken (e.g., via an osteotomy) to create this separation, dividing the bone into a first bone segment and a second bone segment. The cut may be done prior to implanting and securing the adjustable implant 100 or may be done after the adjustable implant 100 is fully or partially implanted, for example by use of a flexible Gigli saw. As will be described herein, the implant 100 is configured such that the second portion 104 can one or both of contract (e.g., for compression) and distract (e.g., for limb lengthening) relative to the first portion 102 along a longitudinal axis ($A_2$) distally or proximally. The adjustable implant 100 is configured to allow controlled, precise translation of the second portion 104 relative to the first portion 102 by non-invasive remote control, and thus controlled, precise translation of the second bone segment coupled to the second portion 104 relative to the first bone segment coupled to the first portion 102.

Over the treatment period for limb lengthening, the bone is regularly distracted, creating a new separation, into which osteogenesis can occur. Regularly distracted is meant to indicate that distraction occurs on a regular or periodic basis which may be on the order of every day or every few days. An exemplary distraction rate is one millimeter per day, although other distraction rates may be employed. That is to say, a typical distraction regimen may include a daily increase in the length of the adjustable implant 100 by about one millimeter. This may be accomplished, for example, by four lengthening periods per day, each providing 0.25 mm of lengthening. The adjustable implant 100 includes a drive assembly 110 configured to drive rotational motion about an axis ($A_1$), which allows the second portion 104 to be telescopically extended from the first portion 102, thus forcing the first and second segments of the bone apart from one another. The rotational axis $A_1$ may be orthogonal to the axis $A_2$, as shown in FIG. 1. In alternative embodiments of the disclosure, the rotational axis $A_1$ and the axis $A_2$ form an oblique angle, as disclosed in more detail below.

Figure 2:
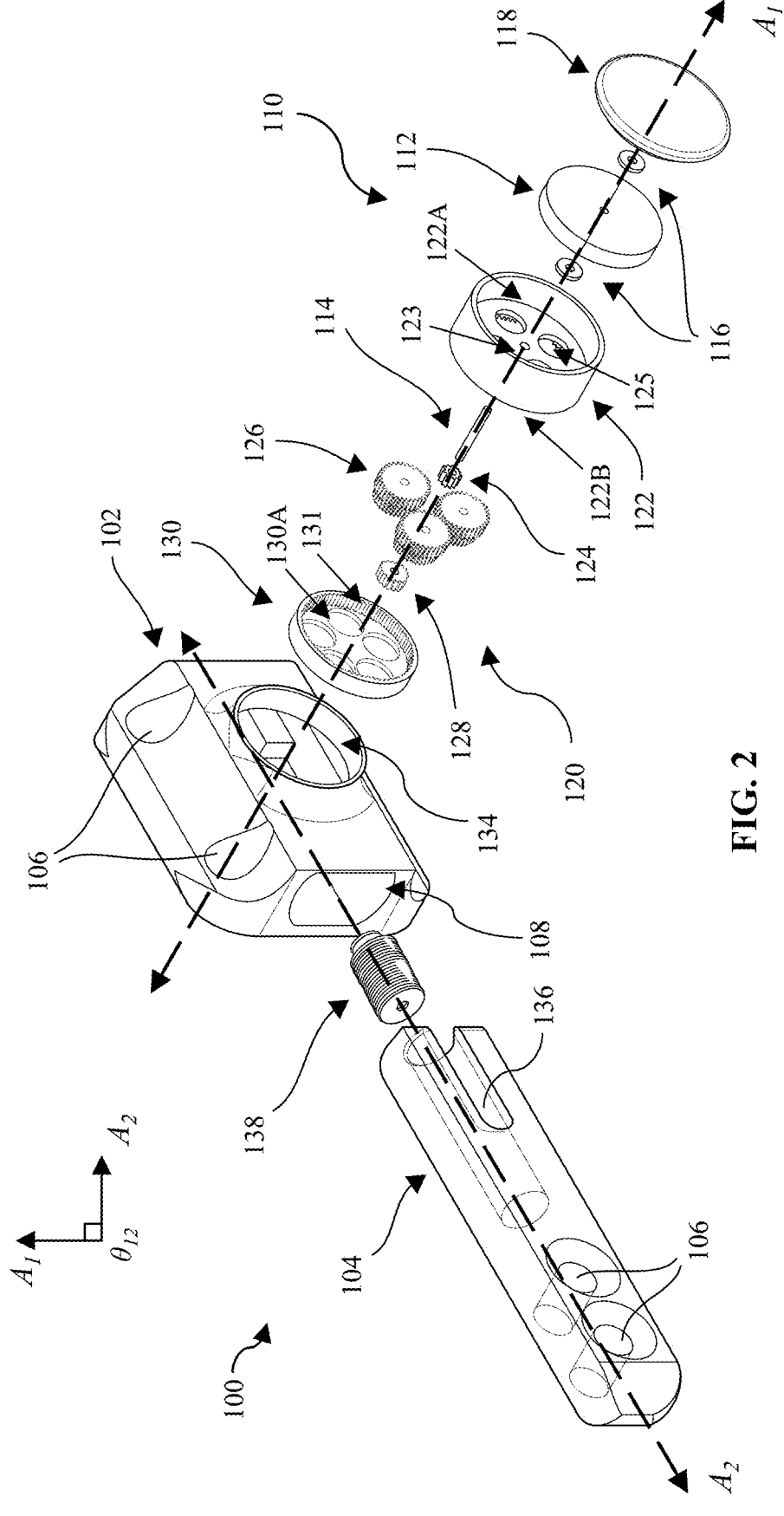
FIG. 2 illustrates an exploded perspective view of the adjustable implant of FIG. 1.

Turning to FIG. 2, the adjustable implant 100 includes a drive assembly 110 at least partially disposed within or coupled to the first portion 102. The drive assembly 110 includes a driver 112 configured to drive rotational motion about the rotational axis $A_1$ of the driver 112. The driver can take any of a variety of forms such as a motor or an externally driven rotatable permanent magnet. The illustrated drive assembly 110 further includes a drive shaft 114 extending proximally from, and rotatably coupled to, the driver 112. The driver 112 and drive shaft 114 may be axially fixed within the first portion 102 by one or more mechanical hardware components such as one or more bearings 116. In the illustrated embodiment, the driver 112 includes a rotatable permanent magnet configured to be rotated by an externally applied magnetic field. An external adjustment device 400 including an external magnet 414, 416 (see FIG. 12) may be configured to actuate rotation of the driver 112 in either of a first direction or a second direction about the rotational axis $A_1$ of the driver 112.

Rotation in the first direction may correspond to distraction of the adjustable implant 100 and rotation in the second direction may correspond to retraction of the adjustable implant 100. For instance, the driver 112 may be configured to rotate about the rotational axis $A_1$ in a first direction corresponding to distal translation of the second portion 104 (e.g., distraction), and to rotate in a second direction opposite the first direction corresponding to proximal translation of the second portion 104 along the axis $A_2$ (e.g., retraction, as in a compression procedure). Alternatively, the adjustable implant may include a motor configured to rotate in response to an electrical signal (e.g., as provided by an external device). The motor may be electrically coupled to a power source such as an implanted battery or charging capacitor to drive rotation of a drive shaft 114. The power source may be configured for transcutaneous charging using an external power source.

Figure 3:
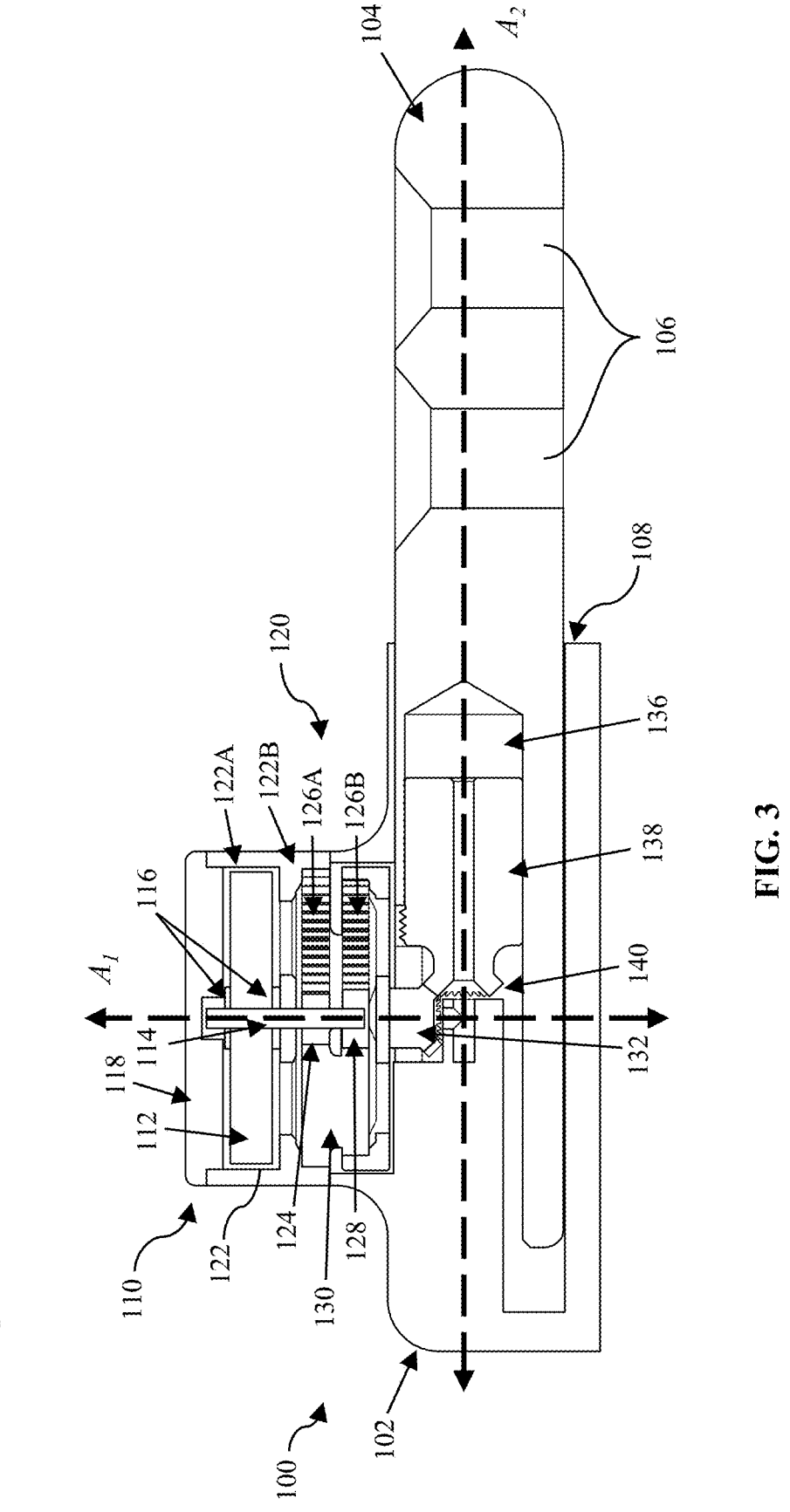
FIG. 3 illustrates a cross-sectional side view of the adjustable implant of FIG. 1.

As further shown by FIGS. 1-3, the adjustable implant 100 further includes a gear assembly 120 (FIGS. 2-3) rotatably coupled to the drive shaft 114 of drive assembly 110. The gear assembly 120 may include a plurality of gears (e.g., one or more output gear, ring gears, sun gears, compound planetary gears, etc.) configured to engage each other to transfer rotational motion from the drive assembly 110 about the axis $A_1$ to rotational motion of a lead screw 138 about the axis $A_2$, thereby causing the second portion 104 to translate along the axis $A_2$, as disclosed in more detail below. The gear assembly 120 may include, for example, a plurality of compound planetary gears 126 disposed about the axis $A_1$ and rotatably coupled to the drive shaft 114, such that rotational motion of the driver 112 causes the plurality of compound planetary gears 126 to rotate about the axis $A_1$. In the embodiment shown in FIGS. 2-3, the gear assembly 120 includes one stage of planetary gears, but it should be understood that any number of stages may be implemented in various embodiments within the scope of the present disclosure. Each stage of the one or more stages of gears in gear assembly 120 may provide a gear reduction ratio such as, e.g., a 66:1 gear reduction ratio. Each compound planetary gear 126 includes a first gear 126A rotatably coupled to a second gear 126B extending proximally from the first gear 126A, such that rotational motion of the drive shaft 114 coupled to sun gear 124 causes the first gears 126A to rotate as a group about the axis $A_1$, thereby causing the second gears 126B as a group to rotate about the axis $A_1$. The first gear 126A of each compound planetary gear is disposed within a first ring gear 122, and the second gear 126B of each compound planetary gear 126 is disposed within a second ring gear 130.

As further shown in FIGS. 2 and 3, the first ring gear 122 of the gear assembly 120 is rotationally fixed to the first portion 102. The first ring gear 122 includes a first cavity 122A configured to receive the driver 112 therein, a second cavity 122B opposite the first cavity 122A along the axis $A_1$, and an aperture 123 configured to receive the drive shaft 114 therein to enable communication between the first cavity 122A and the second cavity 122B. The first ring gear 122 is configured to engage a cover 118 to retain the driver 112 within the first cavity 122A. The second cavity 122B includes an inner surface having a plurality of gear teeth 125 configured to rotatably engage the first gear 126A of each compound planetary gear 126 disposed therein. The first gear 126A of each compound planetary gear 126 may be configured to rotatably engage the plurality of gear teeth 125 in the second cavity 122B, and to rotatably engage a first sun gear 124 coupled to the drive shaft 114, such that rotation of the drive shaft 114 rotates the first sun gear 124, thereby causing the first gear 126A of each compound planetary gear 126 to orbit about the first sun gear 124 within the second cavity 122B. Rotational movement of the first gears 126A of the plurality of compound planetary gears 126 thereby causes rotational movement about the axis $A_1$ of the second gears 126B extending proximally therefrom. The second gear 126B of each compound planetary gear 126 may be configured to be received within, and rotatably engage, a second ring gear 130. The second ring gear 130 includes a cavity 130A configured to receive the second gears 126B therein. The cavity 130A includes an inner surface having a plurality of gear teeth 131 configured to rotatably engage the second gear 126B of each compound planetary gear 126 disposed therein. The second gears 126B orbit about, and rotatably engage, a second sun gear 128 rotatably coupled to a distal end of the drive shaft 114. The second sun gear 128 is configured to support the second gears 126B, but does not provide torque to any gear or component of gear assembly 120 (e.g., second sun gear 128 is an "idling gear"). Rotational movement of the second gears 126B thereby causes the second ring gear 130 to rotate about the axis $A_1$. The second ring gear 130 is rotatably coupled to a beveled output gear 132 (FIGS. 3-4), such that rotation of the second ring gear 130 thereby causes the beveled output gear 132 to rotate about the axis $A_1$. Rotation of the driver 112 therefore rotates the drive shaft 114, which in turn rotates the first sun gear 124, which in turn rotates the plurality of compound planetary gears 126, which in turn rotates the second ring gear 130, and which in turn rotates the beveled output gear 132.

Figure 4:
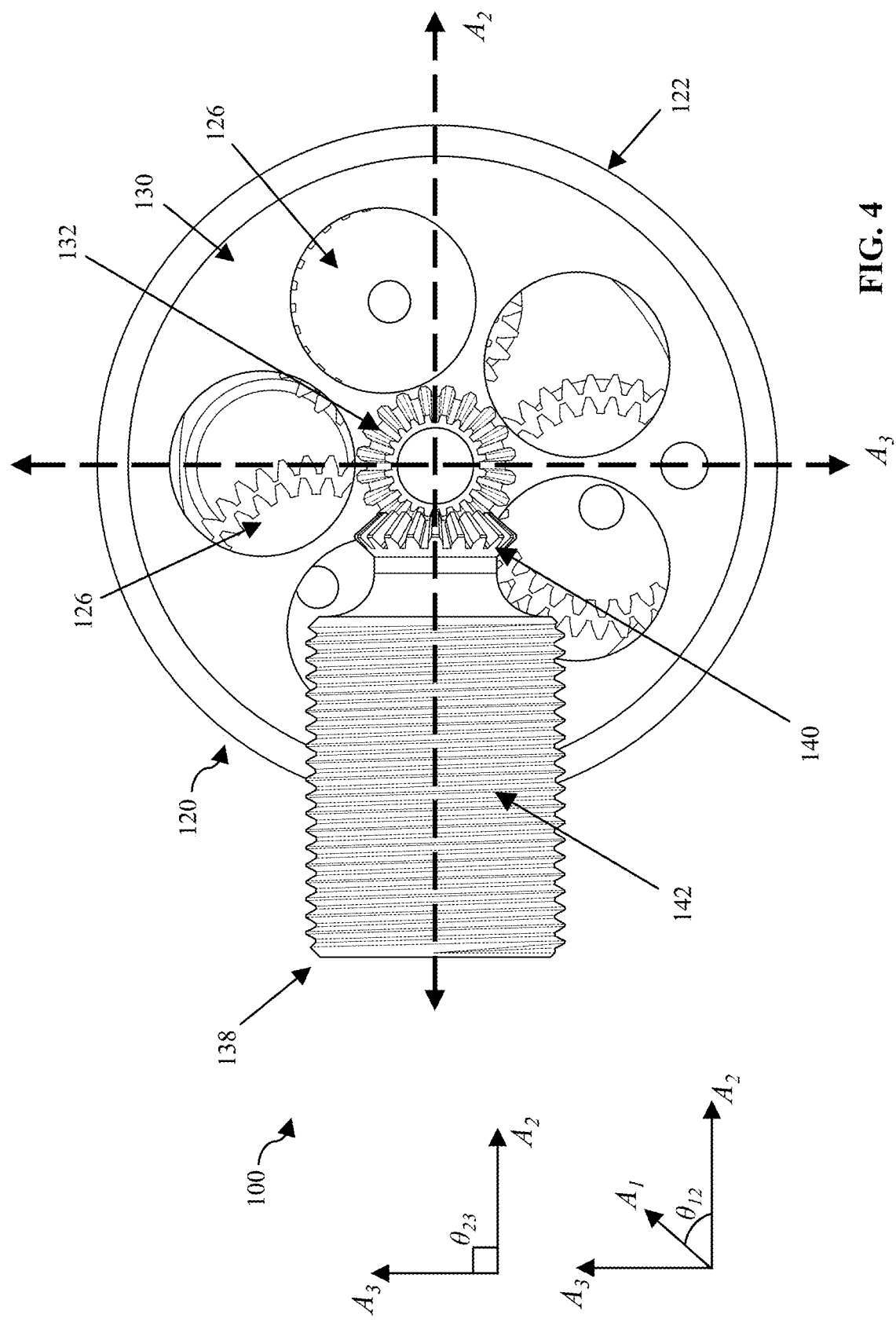
FIG. 4 illustrates a gear assembly and a lead screw of the adjustable implant of FIG. 1.

As shown in FIG. 4, the beveled output gear 132 of the gear assembly 120 is further configured to rotatably engage a lead screw 138, thereby causing the lead screw 138 to rotate about the axis $A_2$, which in turn drives translation of the second portion 104 along the axis $A_2$. As shown, the lead screw 138 includes a shaft extending between a first end having a beveled gear 140 configured to rotatably engage the gear assembly 120, and a second end configured to be received within the second portion 104. The lead screw 138 further includes an externally threaded portion 142 disposed on a radially outward facing surface of the shaft which is configured to threadably engage an internal thread 136 of a cavity 108 within the second portion 104. Rotating the lead screw 138 causes the second portion 104 to translate along the externally threaded portion 142 of the lead screw 138 relative to the first portion 102. Rotation of the lead screw 138 about the axis $A_2$ in the first direction may correspond to distraction of the adjustable implant 100, while rotation in the second direction may correspond to retraction of the adjustable implant 100. The rotational axis $A_1$ of the gear assembly 120 forms an angle which may be, e.g., orthogonal or oblique with the rotational axis $A_2$ of the lead screw 138. In an example, the smallest angle between $A_1$ and $A_2$ is greater than n degrees where n is any integer between 1 degrees and 90 degrees, inclusive. In some embodiments, the lead screw 138 is configured to drive the second portion 104 from the first portion 102 by rotating inside a nut that is secured to an inner surface adjacent to a cavity 108 of the second portion 104 in which the lead screw 138 is disposed. The lead screw 138 therefore is indirectly mechanically coupled to the drive assembly 110, such that rotation of the driver 112 effectuates rotation of the lead screw 138. Rotation of the driver 112 therefore rotates the drive shaft 114, which in turn rotates the beveled output gear 132 of the drive assembly 110 about $A_1$, which in turn rotates the lead screw 138 about axis $A_2$, and which in turn drives axial translation of the second portion 104 relative to the first portion 102.

Figure 5:
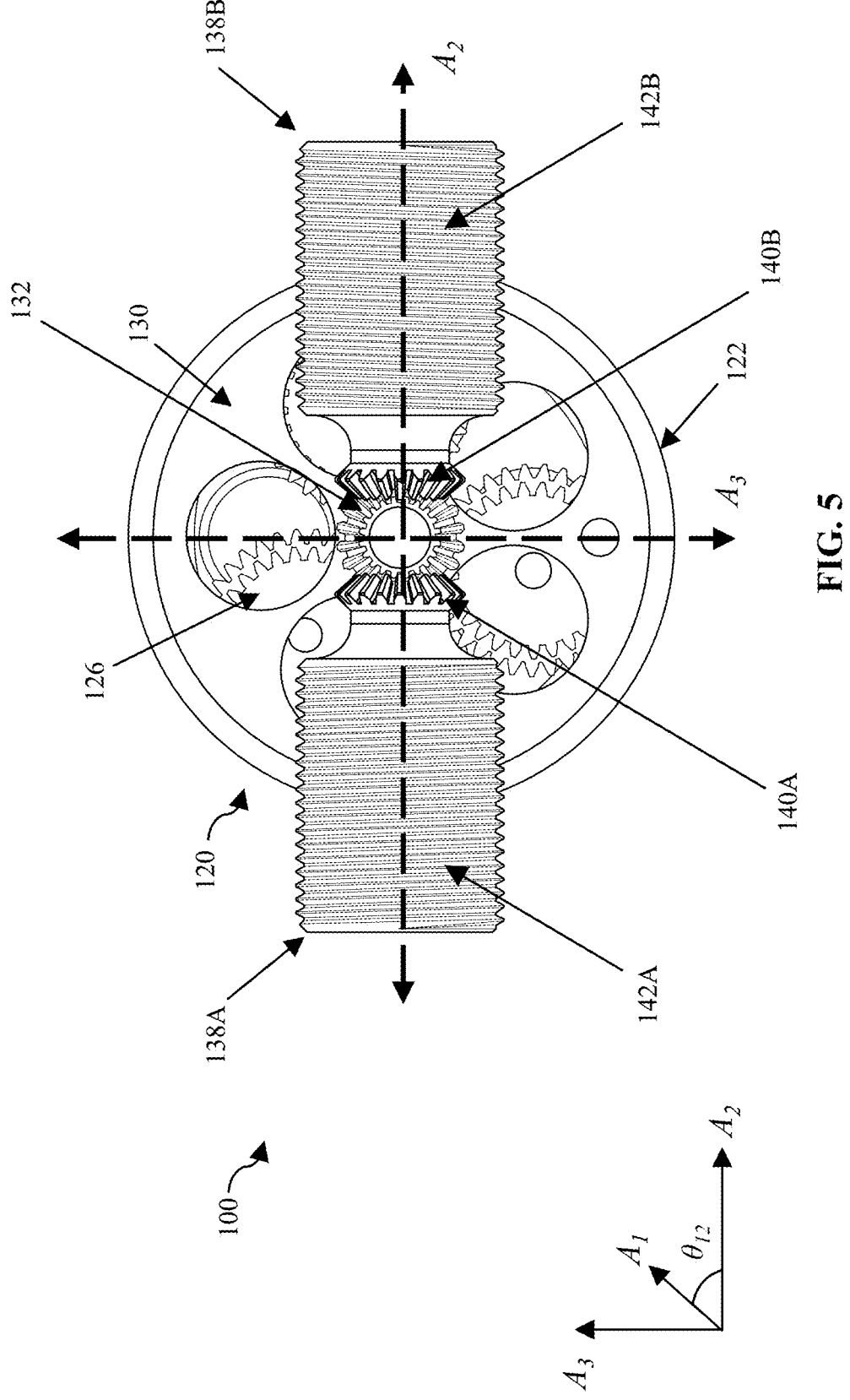
FIGS. 5 and 6 illustrate an embodiment of an adjustable implant including two or more lead screws coupled with the gear assembly.
Figure 6:
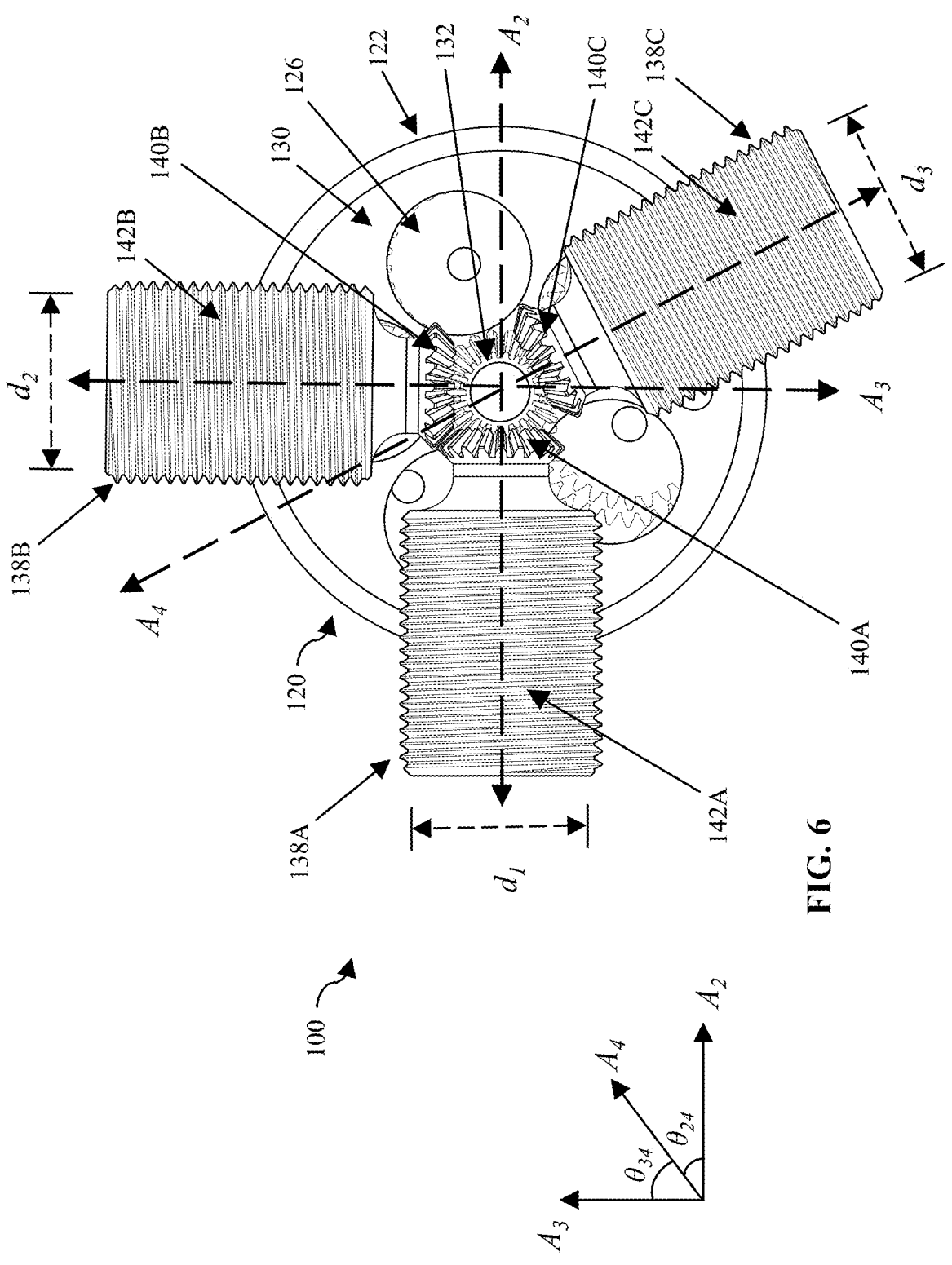

In another embodiment, such as shown in FIGS. 5 and 6, the adjustable implant 100 includes two or more lead screws rotatably coupled to the gear assembly. In such embodiments, each of the two or more lead screws includes a beveled gear configured to rotatably engage the beveled output gear of the gear assembly. The quantity of lead screws that rotatably engage the gear assembly may be determined by the size and shape of the implant, the number of gear teeth on the beveled output gear, and/or the size and shape of each lead screw. The present disclosure is not limited to the number of lead screws shown in the drawings, and encompasses any number of lead screws disposed within an adjustable implant that axially translate in response to rotation of a gear assembly oriented at an angle with respect to the lead screws. In certain embodiments, two or more lead screws may be partially disposed within two or more portions of the adjustable implant (e.g., distraction and compression rods) that are configured to axially translate relative to another portion (e.g., a housing similar to first portion 102 shown in FIGS. 1-3). Rotation of the drive assembly therefore drives rotational motion of each of two or more lead screws, thereby causing two or more portions of the adjustable implant to axially translate along the respective rotational axis of the two or more lead screws relative to the housing. In some embodiments, each lead screw of the two or more lead screws are substantially identical. In other embodiments, one or more lead screws have a different size and/or shape than another one of the lead screws.

In one embodiment, as shown in FIG. 5 for example, the adjustable implant 100 includes two lead screws 138A, 138B configured to matingly engage the beveled output gear 132 and rotate about the same axis $A_2$, thereby causing two portions (not shown) to axially translate along axis $A_2$ in opposite directions. Rotation of the beveled output gear 132 therefore drives rotation of the beveled output gears 140A, 140B of lead screws 138A, 138B, which in turn causes respective portions of the adjustable implant 100 to axially translate via external threads 142A, 142B in opposite directions along the axis $A_2$.

In another embodiment, as shown in FIG. 6 for example, the adjustable implant includes first lead screw 138A, second lead screw 138B, and third lead screw 138C that are configured to matingly engage beveled output gear 132 and rotate about axis $A_2$, axis $A_3$, and axis $A_4$, respectively. Each lead screw 138A, 138B, 138C having a respective beveled gear 140A, 140B, 140C configured to matingly engage the beveled output gear 132. Rotation of the beveled output gear 132 therefore drives rotation of the beveled output gears 140A, 140B, 140C of lead screws 138A, 138B, 138C, which in turn causes respective portions of the adjustable implant 100 to axially translate via external threads 142A, 142B, 142C in different directions along the respective axis $A_2$, $A_3$, $A_4$. Each axis $A_2$, $A_3$, $A_4$ is orthogonal to the rotational axis $A_1$ of beveled output gear 132, and forms an angle (e.g., oblique, orthogonal, etc.) with respect to the other lead screw axis (i.e., $\theta_{34}$ and $\theta_{24}$).

In the examples of FIGS. 5 and 6, the first portion 102 (e.g., the portion of the adjustable implant by which the driver 112 and gear assembly 120 is retained) can be configured to be directly fixed to bone (e.g., by having one or more fixation apertures 106) or can lack a direct bone connection (e.g., by lacking fixation apertures 106). In an example implementation, the two or more lead screws 138 cause respective components fixed to bone (e.g., by having fixation apertures) to translate relative to the first portion.

Figure 7:
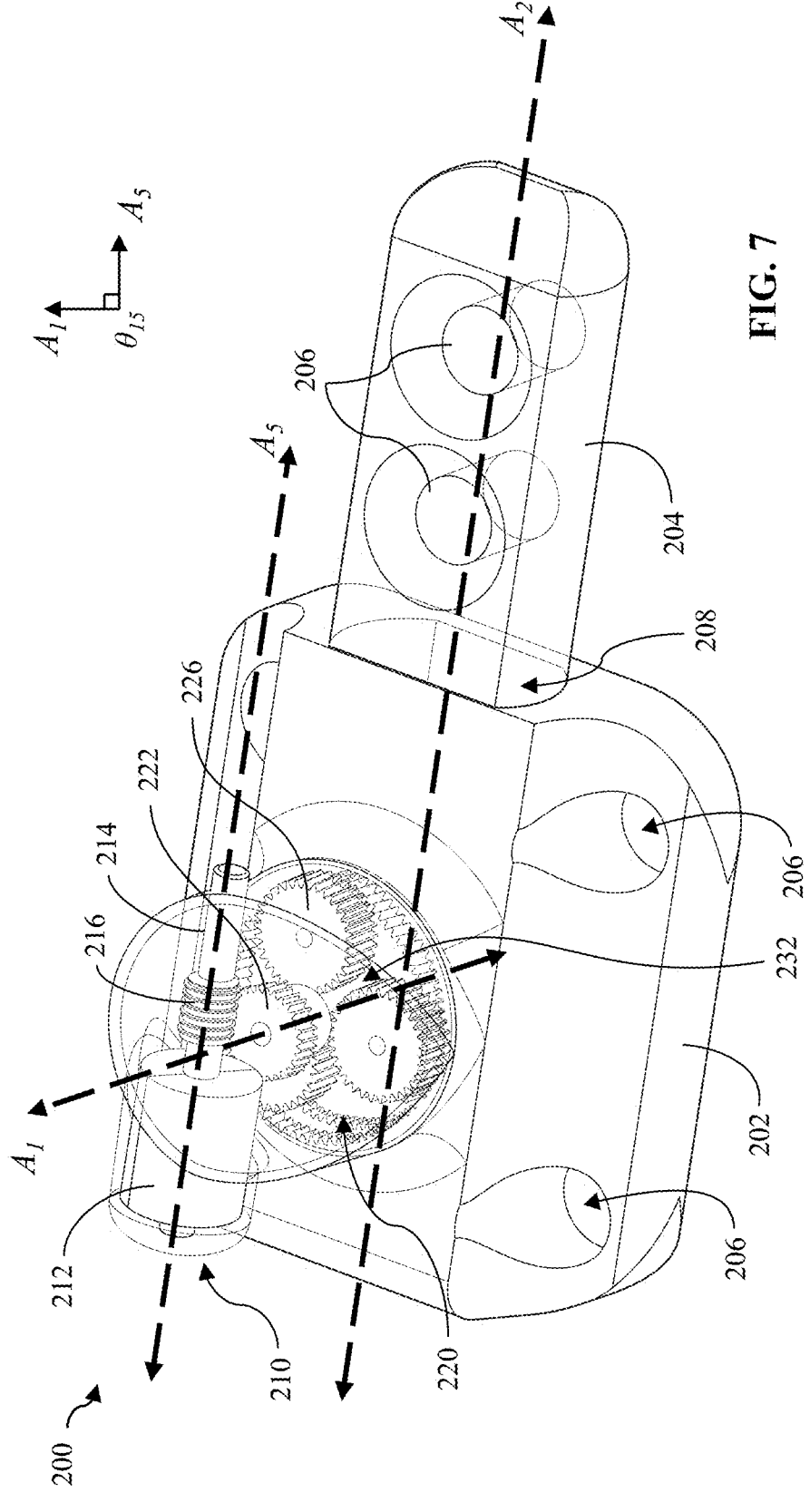
FIG. 7 illustrates an assembled perspective view of an embodiment of an adjustable implant including a worm gear according to the present disclosure.

Turning to FIG. 7, a perspective view is illustrated of another embodiment of an adjustable implant 200 including a drive assembly 210 having a worm gear 216 configured to rotatably engage a gear assembly 220. As shown, the adjustable implant 200 includes a first portion 202 configured to be fixed to a patient's bone at a first location, and a second portion 104 at least partially disposed within the first portion 202 configured to be fixed to the bone at a second location (e.g., a second bone segment). The adjustable implant 200 is configured to allow controlled, precise translation of the second portion 204 relative to the first portion 202 by non-invasive remote control, and thus controlled, precise translation of the second bone segment coupled to the second portion 204 relative to the first bone segment coupled to the first portion 202. In contrast to the embodiment shown in FIGS. 1-3, the drive assembly 210 of the adjustable implant 200 includes a driver 212 (e.g., a rotatable permanent magnet) configured to drive rotational motion of a drive shaft 214 about an axis $A_5$, thereby causing the gear assembly 220 to rotate about an axis $A_1$. The drive shaft 214 includes a worm gear 216 configured to matingly engage an input gear 222 of the gear assembly 220, which in turn causes a plurality of planetary gears 226 of the gear assembly 220 to rotate about the axis $A_1$, thereby causing an output gear 232 of the gear assembly 220 to rotate about the axis $A_1$. The gear assembly 220 is configured to transfer rotational motion from the drive assembly 210 to a lead screw (not shown) disposed within the first portion 202 in a manner similar to the gear assembly 120 described with respect to FIGS. 1-4, details of which have been omitted herein for brevity. It should be noted that other gear assembly designs configured to transfer rotational motion from the drive assembly 210 to the lead screw are also contemplated within the scope of this invention. Rotation of the driver 212 therefore causes the drive shaft 214 to rotate about the axis $A_5$, which in turn rotates the worm gear 216 about the axis $A_5$, which in turn rotates the input gear 222 about the axis $A_1$, which in turn rotates the plurality of planetary gears 226 about the axis $A_1$, which in turn rotates the output gear 232 about the axis $A_1$, which in turn causes the lead screw to rotate about an axis $A_2$, and which in turn causes the second portion 204 to axially translate along the axis $A_2$ relative to the first portion 202. In some embodiments, the axis $A_5$ of the drive assembly 210 is orthogonal to the axis $A_1$ of the gear assembly 220. In other embodiments, the axis $A_5$ of the drive assembly 210 forms an oblique angle with the axis $A_1$ of the gear assembly 220.

Figure 8:
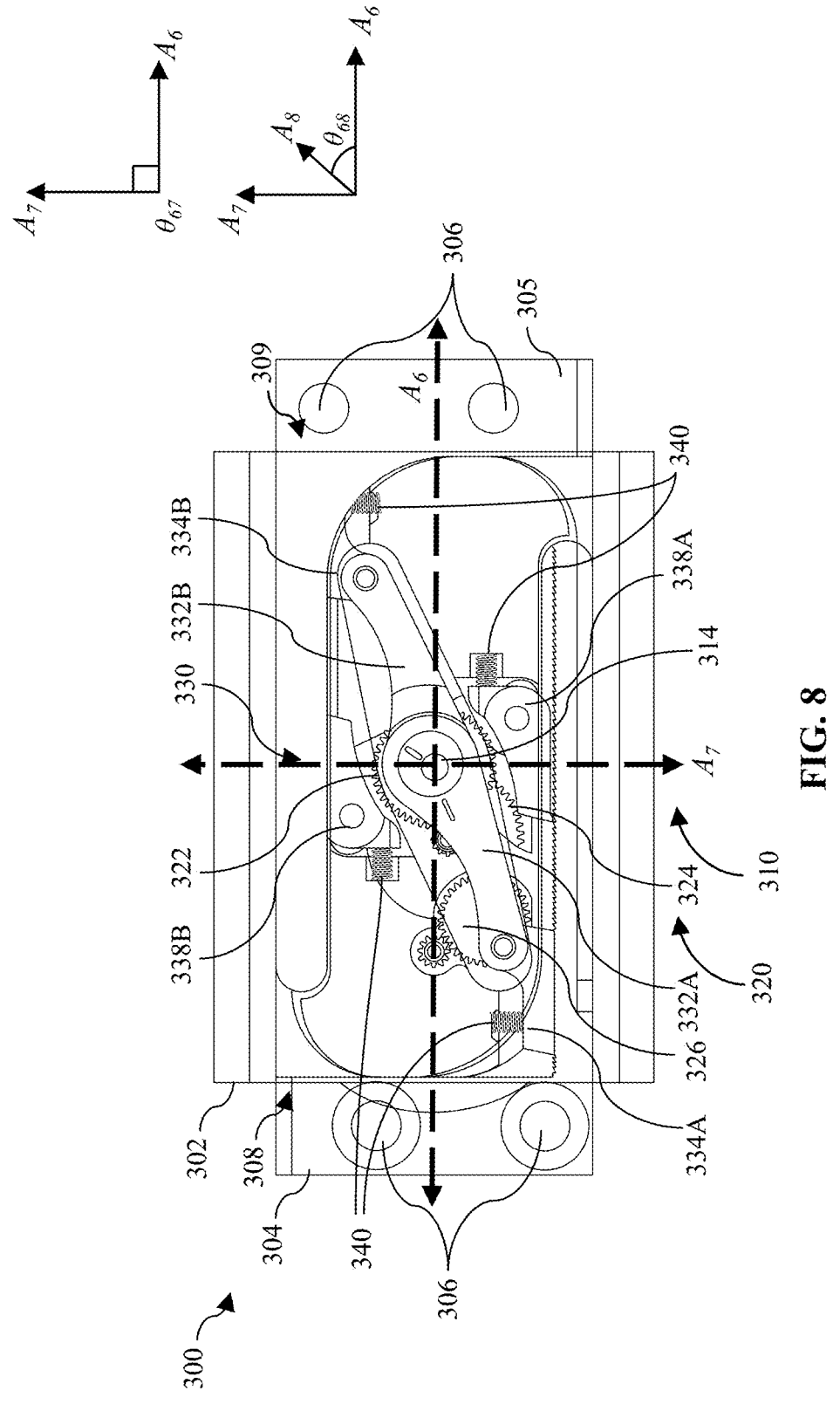
FIG. 8 illustrates a cross-sectional top view of an embodiment of an adjustable implant including a ratchet assembly and bi-directional plates according to the present disclosure.
Figure 9:
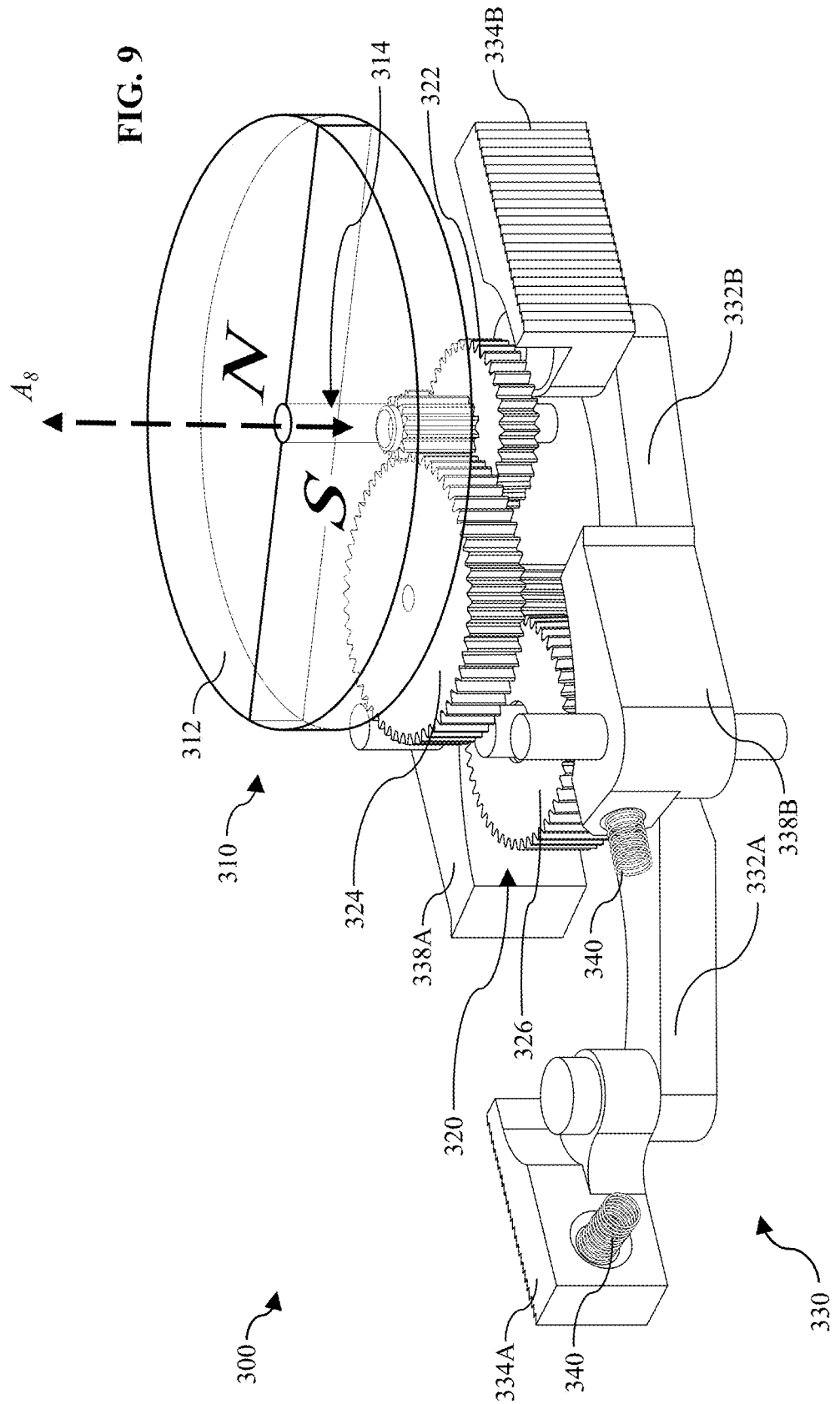
FIG. 9 illustrates a cross-sectional perspective view of the adjustable implant of FIG. 8.
Figure 10:
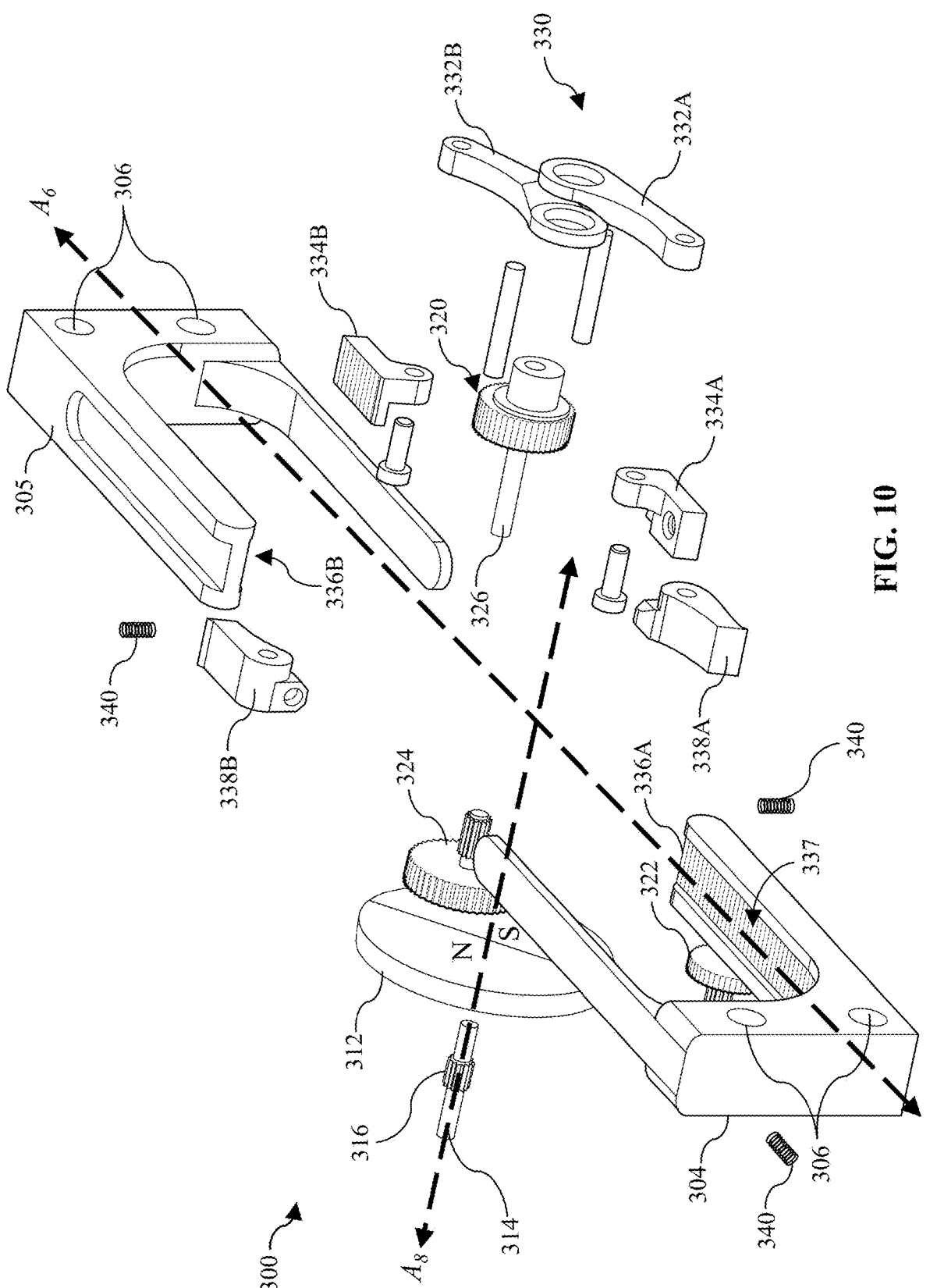
FIG. 10 illustrates an exploded cross-sectional perspective view of the adjustable implant of FIG. 8.

As shown in FIGS. 8-10, an adjustable implant 300 according to another embodiment includes a first portion 302 (e.g., a housing) configured to receive a second portion 304 and a third portion 305 therein. Two or more of portions 302, 304, 305 can include a flat plate shaped and dimensioned to engage a bone of a patient at respective locations. For example, the first portion 302 can (but need not) be configured to be fixed to bone at a first location (e.g., a first bone segment). The second portion 304 can be configured to be fixed to bone at a first or second location (e.g., a first or second bone segment). The third portion 305 can be configured to be fixed to the bone at a second or third location (e.g., a second or third bone segment). Each portion 302, 304, 305 can further include one or more fixation apertures 306 configured to receive one or more fixation screws therein that are configured to couple each portion 302, 304, 305 to the respective location of the bone. As will be described herein, the second portion 304 is configured to distract relative to the first portion 302 along a longitudinal axis $(A_6)$ in a first direction, and the third portion 305 is configured to distract relative to the first portion 302 along the longitudinal axis $A_6$ in a second, opposite direction. The adjustable implant 300 is configured to allow controlled, precise translation of the second and third portions 304, 305 relative to the first portion 302 by non-invasive remote control, and thus controlled, precise translation of the second and third bone segments along the longitudinal axis $A_6$ relative to the first bone segment.

Turning to FIGS. 9-10, additional internal features of the adjustable implant 300 are shown. The adjustable implant 300 includes a drive assembly 310 at least partially disposed within the first portion 302 (FIG. 8). The drive assembly 310 includes a driver 312 configured to drive rotational motion about the rotational axis $A_8$ of the driver 312 such as, e.g., a rotatable permanent magnet or motor. The drive assembly 310 further includes a drive shaft 314 extending proximally from, and rotatably coupled to, the driver 312. The driver 312 and drive shaft 314 may be axially fixed within the first portion 302 by one or more mechanical hardware components. Drive assembly 310 may further include a driver output gear 316 disposed along the drive shaft 314. As shown in FIGS. 9-10, the driver 312 may include a rotatable permanent magnet configured to be rotated by an externally applied magnetic field. An external adjustment device 400 including an external magnet 414, 416 (see FIG. 12) may be configured to actuate rotation of the driver 312 in either of a first direction or a second direction about the rotational axis $A_5$ of the driver 312. Rotation in at least one of the first direction or the second direction may correspond to, for example, distraction of the second and third portions 304, 305 along the axis $A_6$ relative to the first portion 302. Alternatively, the adjustable implant 300 may include a motor configured to rotate in response to an electrical signal (e.g., as provided by an external device). The motor may be electrically coupled to a power source such as, e.g., a battery or charging capacitor, to drive rotation of a drive shaft. The power source may be configured for transcutaneous charging using an external power source.

As further shown by FIGS. 9-10, the adjustable implant 300 further includes a gear assembly 320 rotatably coupled to the drive assembly 310 via the driver output gear 316. The gear assembly 320 includes a plurality of gears (e.g., input gear, output gear, etc.) configured to engage each other to transfer rotational motion from the driver 312 about the axis $A_8$ to a ratchet assembly 330 disposed along an axis $A_6$. This causes the ratchet assembly 330 to actuate axial translation of the second and third portions 304, 305 relative to the first portion 302, as discussed herein. Gear assembly 320 may include, for example, an input gear 322 rotatably coupled to the drive shaft 314, an output gear 324 configured to rotatably engage the input gear 322, and an eccentric shaft 326 configured to rotatably engage the output gear 324. Rotation of the driver 312 therefore rotates the drive shaft 314, which in turn rotates the input gear 322, which in turn rotates the output gear 324, and which in turn rotates the eccentric shaft 326. The eccentric shaft 326 is coupled with the ratchet assembly 330, such that rotation of the eccentric shaft 326 actuates the ratchet assembly 330.

In some embodiments, as shown in FIGS. 8-10, the ratchet assembly 330 includes a first ratchet arm 332A and a second ratchet arm 332B, each of which is disposed within the first portion 302 and rotatably coupled with the eccentric shaft 326. The first and second ratchet arms 332A, 332B are configured to rotate within the first portion 302 about the eccentric shaft 326 in response to rotation of the drive assembly 310, thereby causing the second and third portions 304, 305, respectively, to axially translate along the axis $A_6$ (FIG. 8) relative to the first portion 302. The first ratchet arm 332A includes a first end coupled to a first ratchet 334A and a second end rotatably coupled to the eccentric shaft 326. The second ratchet arm 332B includes a first end coupled to a second ratchet 334B and a second end rotatably coupled to the eccentric shaft 326. As shown in FIG. 10, the ratchet assembly 330 further includes a first linear rack 336A disposed on the second portion 304 and a second linear rack 336B disposed on the third portion 305. Each of the first and second linear racks 336A, 336B may have a plurality of ratchet teeth 337 configured to engage the first and second ratchets 334A, 334B, respectively, to incrementally drive axial translation along the axis $A_6$. The ratchet assembly 330 further includes a first pawl 338A configured to engage the first linear rack 336A and a second pawl 338B configured to engage the second linear rack 336B. The first and second pawls 338A, 338B are dimensioned to allow distraction of the second and third portions 304, 305, respectively, in a first direction along the axis $A_6$, yet inhibit retraction of the second and third portions 304, 305, respectively, in a second direction opposite the first direction. The ratchet assembly 330 may further include mechanical hardware such as, e.g., springs 340, that are configured to position the ratchets 334A, 334B and/or pawls 338A, 338B within the ratchet teeth 337 of respective linear racks 336A, 336B in the absence of rotational movement from the drive assembly 310. Rotation of the driver 312 therefore rotates the drive shaft 314, which in turn rotates the input gear 322, which in turn rotates the output gear 324, which in turn rotates the eccentric shaft 326, and which in turn causes the ratchet assembly 330 to actuate axial translation of the second and third portions 304, 305 along the axis $A_6$ relative to the first portion 302.

Figure 11:
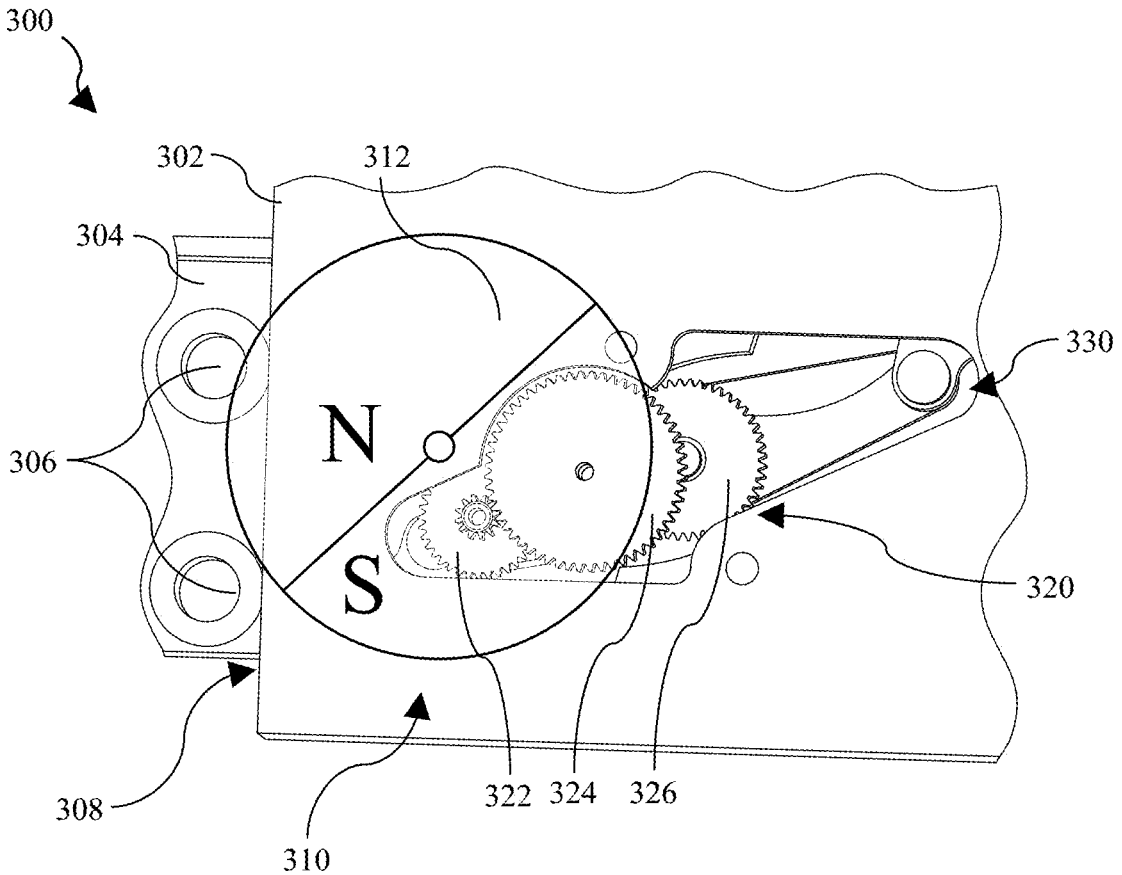
FIG. 11 illustrates a cross-sectional top view of an embodiment of an adjustable implant including a ratchet assembly according to the present disclosure.

As shown in FIG. 11, in some embodiments, the adjustable implant 300 includes a ratchet assembly 330 configured to actuate axial translation of the second portion 304 relative to the first portion 302. In contrast to the embodiment shown in FIGS. 8-10, the adjustable implant 300 of FIG. 11 does not include the third portion 305 and related components of the ratchet assembly 330 that are configured to engage the third portion 305.

Figure 12:
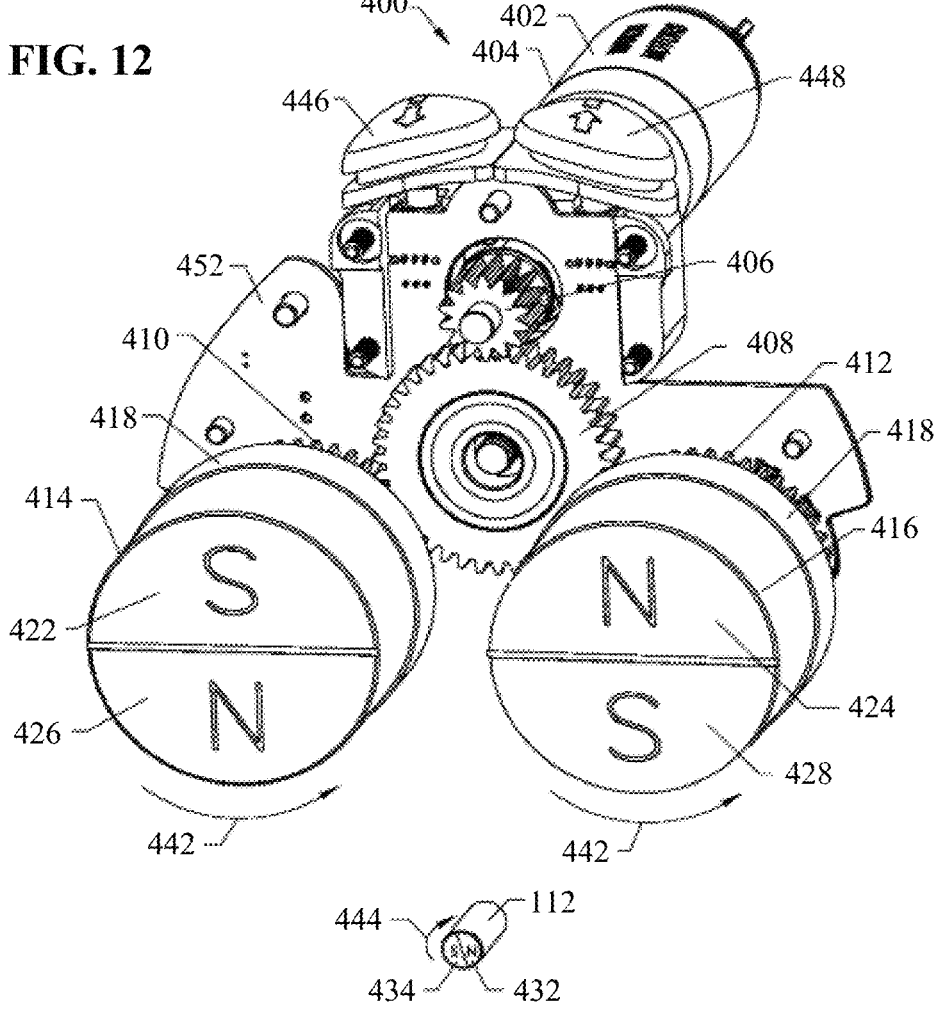
FIG. 12 shows the internal components of an external adjustment device for non-invasively adjusting a distraction and compression device according to embodiments of the invention.
Figure 13:
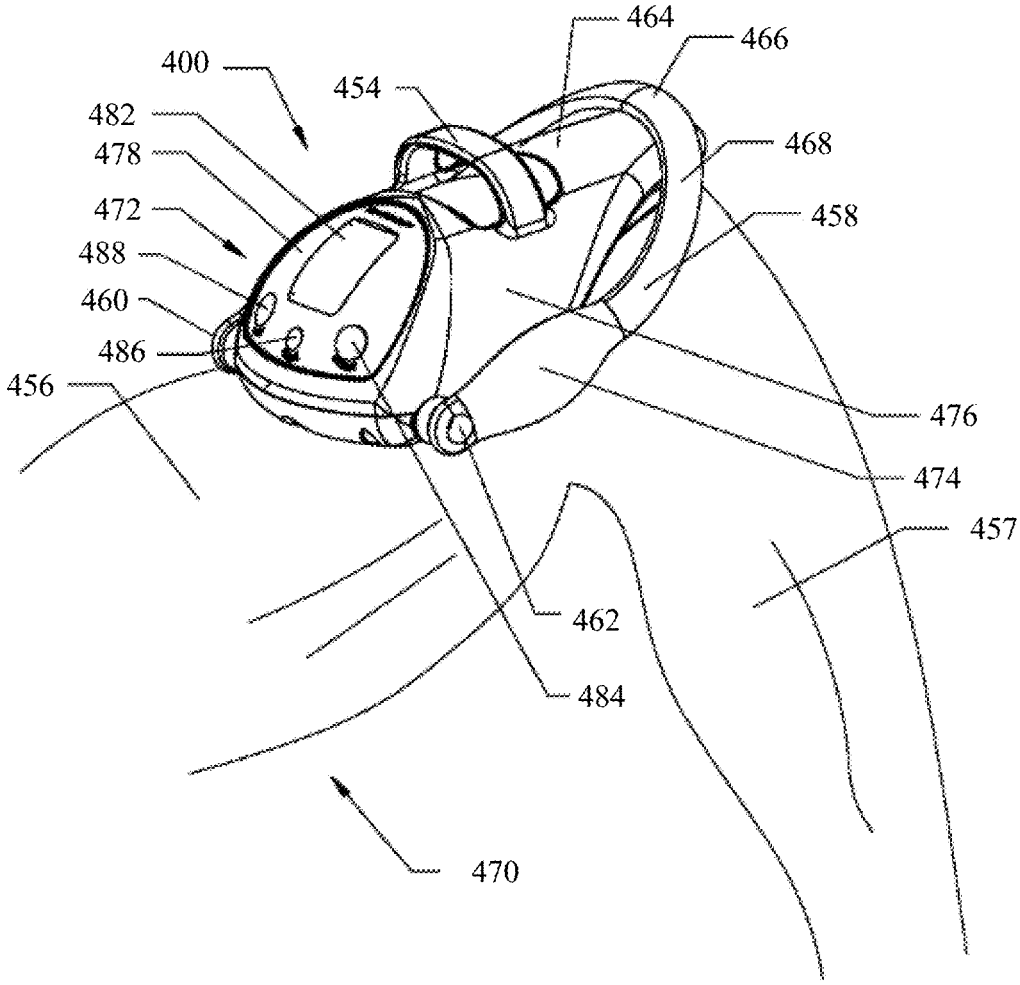
FIGS. 13 and 14 show external adjustment devices in configurations for adjusting a distraction and compression device implanted within a femur, and within a tibia, respectively, in accordance with embodiments of the invention.
Figure 14:
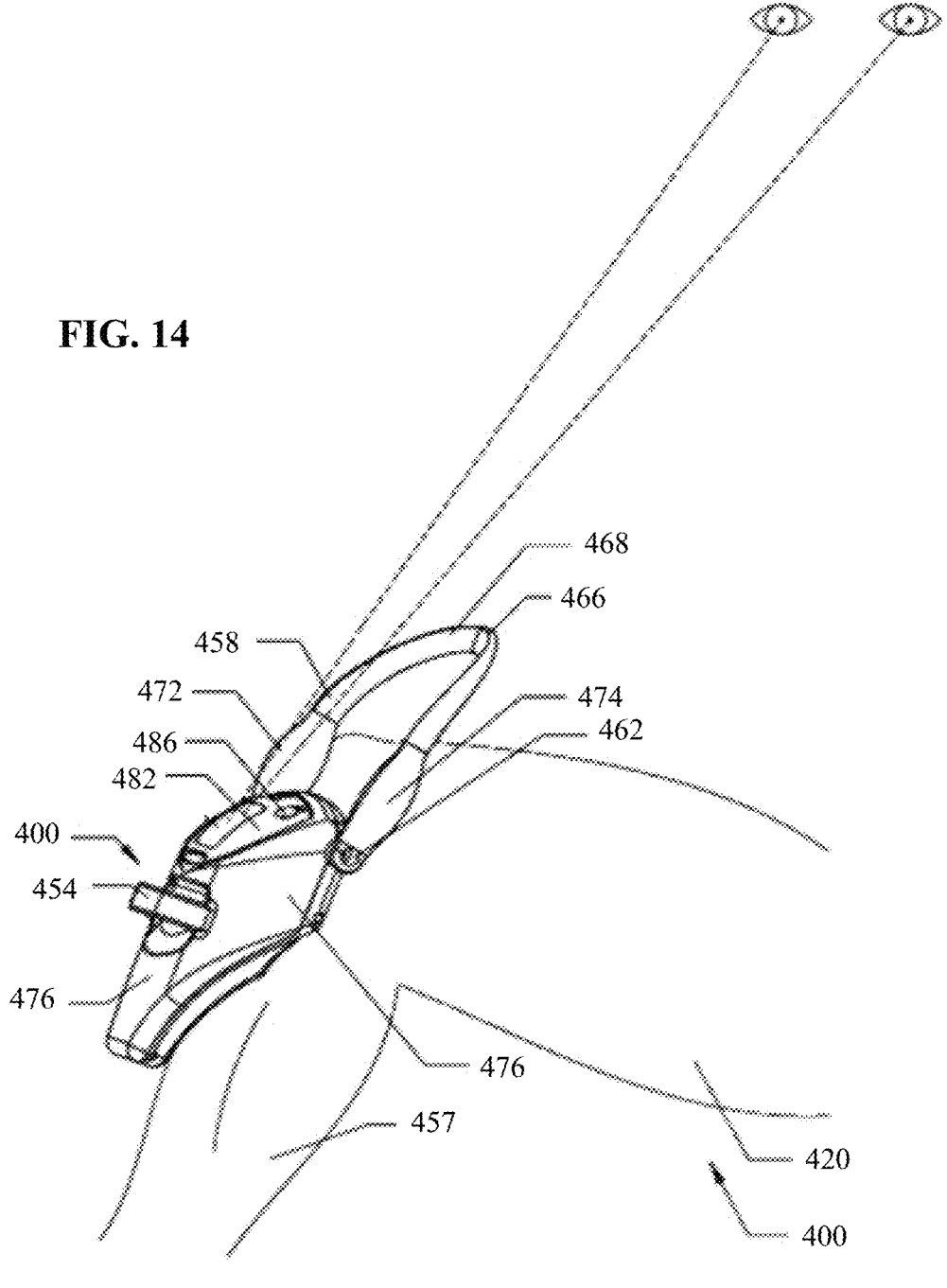

FIGS. 12-14 illustrate an external adjustment device 400 configured for applying a moving magnetic field to allow for non-invasive adjustment of the adjustable implant 100, 200, 300 by turning a driver 112, 212, 312 within the adjustable implant 100, 200, 300, as described. External adjustment device 400 may also be referred to as an external remote controller or external remote control device, and may operate analogously with respect to drive assembly 110, 210, 310 of the adjustable implant 100, 200, 300. FIG. 12 illustrates the internal components of the external adjustment device 400, and for clear reference, shows the driver 112 of the adjustable implant 100 (as representative of drivers 112, 212, 312 and implant systems 100, 200, 300 disclosed herein) without the rest of the assembly. The internal working components of the external adjustment device 400 may, in certain embodiments, be similar to those described in U.S. Patent Application Publication No. 2012/0004494, which is incorporated by reference herein. A motor 402 with a gear box 404 outputs to a motor gear 406. The motor gear 406 engages and turns central (idler) gear 408, which has the appropriate number of teeth to turn first and second magnet gears 410, 412 at identical rotational speeds. First and second magnets 414, 416 turn in unison with the first and second magnet gears 410, 412, respectively. Each magnet 414, 416 is held within a respective magnet cup 418 (shown partially). An exemplary rotational speed may be 60 RPM or less. This speed range may be configured to limit the amount of current density induced in the body tissue and fluids, to meet international guidelines or standards. As seen in FIG. 12, the south pole 422 of the first magnet 414 is oriented the same as the north pole 424 of the second magnet 416, and likewise, the first magnet 414 has its north pole 426 oriented the same as the south pole 428 of the second magnet 416. As these two magnets 414, 416 turn synchronously together, they apply a complementary and additive moving magnetic field to the radially-poled driver 112, having a north pole 432 and a south pole 434. Magnets having multiple north poles (for example, two) and multiple south poles (for example, two) are also contemplated in each of the devices. As the two magnets 414, 416 turn in a first rotational direction 442 (e.g., counter-clockwise), the magnetic coupling causes the driver 112 to turn in a second, opposite rotational direction 444 (e.g., clockwise). The rotational direction of the motor 402 and corresponding rotational direction of the magnets 414, 416 is controlled by buttons 446, 448. One or more circuit boards 452 contain control circuitry for both sensing rotation of the magnets 414, 416 and controlling the rotation of the magnets 414, 416.

FIGS. 13 and 14 show the external adjustment device 400 for use with a device placed in the femur (FIG. 13) or the tibia (FIG. 14). The external adjustment device 400 has a first handle 454 for carrying or for steadying the external adjustment device 400, for example, steadying it against an upper leg 456 (as in FIG. 13) or lower leg 457 (as in FIG. 14). An adjustable handle 458 is rotationally attached to the external adjustment device 400 at pivot points 460, 462.

Pivot points 460, 462 have easily lockable/unlockable mechanisms, such as a spring-loaded brake, ratchet, or tightening screw, so that a desired angulation of the adjustable handle 458 in relation to housing 464 can be adjusted and locked in orientation. In FIG. 13, adjustable handle 458 is set so that apex 466 of loop 468 rests against housing 464. In this position, patient 470 is able to hold onto one or both of grips 472, 474 while the adjustment procedure (for example transporting bone between 0.10 mm to 1.50 mm) is taking place. It is contemplated that the procedure could also be a lengthening procedure for a bone lengthening device or a lengthening procedure for a lengthening plate which is attached external to the bone. Turning to FIG. 14, when the adjustable implant 100 is implanted in a tibia, the adjustable handle 458 may be changed to a position in which the patient 470 can grip onto the apex 466 so that the magnet area 476 of the external adjustment device 400 is held over the portion of the adjustable implant 100 containing the driver 112. In both cases, the patient 470 is able to clearly view control panel 478 including a display 482. In a different configuration from the two directional buttons 446, 448 in FIG. 12, the control panel 478 includes a start button 484, a stop button 486 and a mode button 488. Control circuitry contained on circuit boards 452 may be used by the surgeon to store important information related to the specific aspects of each particular patient. For example, in some patients an implant may be placed antegrade into the tibia. In other patients the implant may be placed either antegrade or retrograde about the femur. In each of these three cases, it may be desired to move the bone either from distal to proximal or from proximal to distal. By having the ability to store information of this sort that is specific to each particular patient within the external adjustment device 400, the external adjustment device 400 can be configured to direct the magnets 414, 416 to turn in the correct direction automatically, while the patient need only place the external adjustment device 400 at the desired position, and push the start button 484. The information of the maximum allowable bone transport length per day and maximum allowable bone transport length per session can also be input and stored by the surgeon for safety purposes. These may also be added via an SD card or USB device, or by wireless input. An additional feature is a camera at the portion of the external adjustment device 400 that is placed over the skin. For example, the camera may be located between the first magnet 414 and second magnet 416. The skin directly over the implanted driver 112 may be marked with indelible ink. A live image from the camera is then displayed on the display 482 of the control panel 478, allowing the user to place the first and second magnets 414, 416 directly over the area marked on the skin. Crosshairs can be overlaid on the display 482 over the live image, allowing the user to align the mark on the skin between the crosshairs, and thus optimally place the external adjustment device 400.

Other external adjustment devices can be used to cause actuation of the distraction devices described herein. Such external adjustment devices include, for example, those described in U.S. Pat. No. 8,382,756 filed on Nov. 20, 2009, U.S. Pat. No. 9,248,043 filed Jun. 29, 2011, U.S. Pat. No. 9,078,711 filed on Jun. 6, 2012, U.S. Pat. No. 9,044,281 filed on Oct. 18, 2012, U.S. application Ser. No. 14/698,665 filed on Apr. 28, 2015, U.S. application Ser. No. 14/932,904 filed on Nov. 4, 2015, U.S. Ser. No. 16/004,099 filed on Dec. 12, 2016, and App. No. PCT/US2020/017338 filed on Feb. 7, 2020, all of which are incorporated herein by reference as if set forth in their entirety.

Examples described herein can benefit from techniques described in other applications. In an example, the maintenance feature described in U.S. Pat. No. 10,405,891 (filed Sep. 8, 2017, as U.S. application Ser. No. 15/699,711, which is incorporated herein by reference in its entirety for any and all purposes) can be adapted for use with examples herein. In an example, a modified keeper mechanism described in U.S. application Ser. No. 17/806,552, (filed Jun. 13, 2022, which is incorporated herein by reference in its entirety for any and all purposes) can be adapted for use with examples herein.

Figure 15:
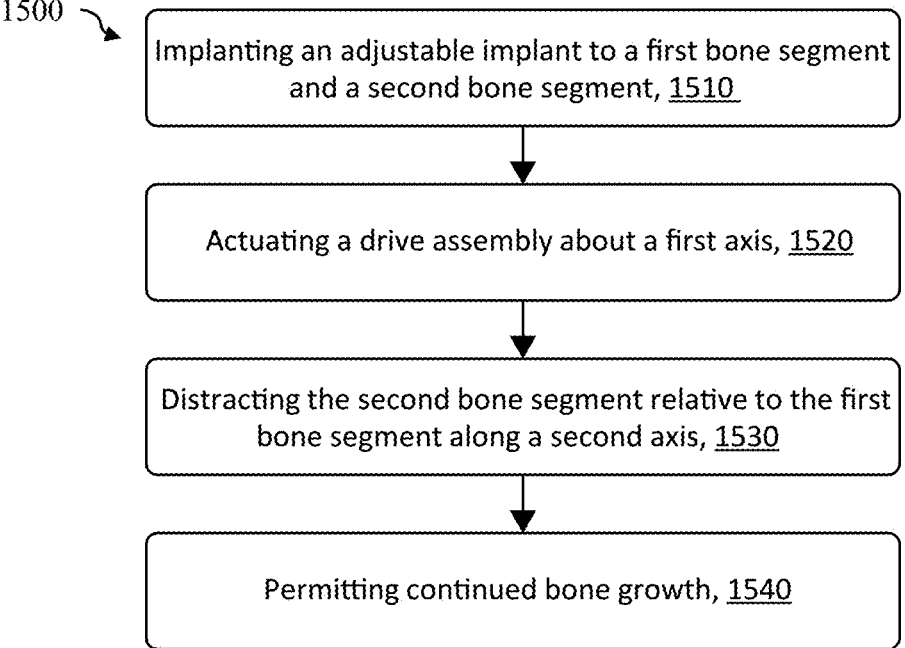
FIG. 15 illustrates a method according to embodiments of the disclosure.

In some embodiments, the present disclosure provides a method of distraction osteogenesis by post-operatively and non-invasively actuating an actuator of a distraction device implanted in a patient. Actuating the actuator of the distraction device may occur transcutaneously through intact skin. The method may further include implanting the distraction device in the patient, and implanting one or more fixation anchors to couple the distraction device to bone segments of the patient. The method may include forming one or more incisions in the patient to implant the distraction device or fixation anchor(s) through the one or more incisions. The method may further include rotating one or more internal magnets of the distraction device by rotating one or more external magnets of an external adjustment device, thereby post-operatively and non-invasively actuating the actuator. For instance, as shown in FIG. 15, a method 1500 of the present disclosure may include the steps of: implanting 1510 an adjustable implant to a first bone segment and second bone segment; actuating 1520 a drive assembly about a first axis; distracting 1530 the second bone segment relative to the first bone segment along a second axis; and permitting 1540 continued bone growth.

While implementations above are primarily in the context of externally magnetically driven adjustable implant systems, other drive systems can also be used. For example, in addition to or instead of the magnet-based driving, one or more of the drive elements can take the form of an implanted electric motor. The implanted electric motor can be powered by an external power source (e.g., via a radiofrequency link, via an ultrasonic energy transfer technique, via an inductive connection, via another technique, or via combinations thereof) or an implanted power source (e.g., a battery or charging capacitor, which may be charged by the external power source). The implanted power source may be within the implant (e.g., within a housing thereof) or separate from the implant and coupled to the implant via a cable.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on,"

above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure. Further, an embodiment or implementation described herein as "exemplary" is not to be construed as preferred or advantageous, for example, over other embodiments or implementations; rather, it is intended reflect or indicate the embodiment(s) is/are "example" embodiment(s).

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. An adjustable implant comprising:
a first portion configured to couple to a first bone segment;
a drive assembly comprises a driver disposed within the first portion and configured to drive rotational motion about a first axis;
a second portion configured to couple to a second bone segment and axially translate relative to the first portion along a second axis; and
a lead screw disposed at least partially within the first and second portions along the second axis,
wherein the lead screw is rotatably coupled to the drive assembly such that rotational motion about the first axis drives rotational motion of the lead screw about the second axis, thereby causing the second portion to axially translate along the second axis relative to the first portion,
wherein the driver comprises a rotatable permanent magnet configured to be rotated by an externally applied magnetic field,
wherein the first axis and the second axis intersect, and
wherein the first axis and the second axis form an oblique angle.

2. The adjustable implant of claim 1, wherein the first axis is orthogonal to the second axis.

3. The adjustable implant of claim 1, wherein the drive assembly further comprises:
a drive shaft rotatably coupled to the driver, and
wherein the driver is configured to rotate about the first axis in a first direction corresponding to proximal translation of the second portion and in a second direction corresponding to distal translation of the second portion.

4. The adjustable implant of claim 3, further comprising a gear assembly rotatably coupled to the drive shaft, wherein the gear assembly is configured to rotatably engage the lead screw to drive rotational motion of the lead screw about the second axis.

5. The adjustable implant of claim 4, wherein the gear assembly comprises a beveled output gear, and the lead screw comprises a beveled gear configured to matingly engage the beveled output gear.

6. The adjustable implant of claim 5, wherein the gear assembly further comprises:
a first ring gear rotationally fixed to the first portion of the distraction device;
a first sun gear disposed within the first ring gear and rotatably coupled to the drive shaft;
a second sun gear rotatably coupled to a distal end of the drive shaft;
a plurality of compound planetary gears disposed about the first axis, wherein each compound planetary gear comprises a first gear configured to engage the first sun gear, and a second gear configured to engage the second sun gear; and
a second ring gear configured to receive and rotatably engage the second gears of the plurality of compound planetary gears,
wherein the beveled output gear is rotatably coupled to the second ring gear, such that rotation of the second ring gear about the first axis causes rotation of the beveled output gear about the first axis, and rotation of the beveled output gear about the first axis is configured to drive rotational motion of the lead screw about the second axis.

7. The adjustable implant of claim 6, wherein the first ring gear comprises a first cavity configured to receive the driver therein, a second cavity configured to receive the first gears of the plurality of compound planetary gears therein, and an aperture dimensioned to receive the drive shaft therein to enable communication between the first cavity and the second cavity.

8. The adjustable implant of claim 1, further comprising:
a third portion configured to couple to a third bone segment and axially translate along a third axis relative to the first portion;
a second lead screw disposed at least partially within the first and third portions along the third axis,
wherein the second lead screw is configured to rotatably engage the drive assembly to drive rotational motion of the second lead screw about the third axis, thereby causing the third portion to axially translate along the third axis relative to the first portion.

9. The adjustable implant of claim 1, further comprising:
a first fixation anchor configured to couple the first portion of the distraction device to the first bone segment; and
a second fixation anchor configured to couple the second portion of the distraction device to the second bone segment,

wherein each of the first portion and the second portion comprise a receiving aperture configured to receive the first fixation anchor and the second fixation therein, respectively.

10. An adjustable implant comprising:
a first portion configured to couple to a first bone segment;
a gear assembly disposed in the first portion;
a drive assembly configured to rotatably engage the gear assembly and to rotate about a first axis, wherein the drive assembly is configured to drive rotational motion of the gear assembly about a second axis;
a lead screw disposed at least partially within the first portion, and extending along a third axis; and
a second portion configured to couple to a second bone segment, wherein the lead screw is at least partially disposed within the second portion,
wherein the lead screw is rotatably coupled to the drive assembly such that rotational motion of the drive assembly about the first axis drives rotational motion of the gear assembly about the second axis, which drives rotational motion of the lead screw about the third axis, thereby causing the second portion to axially translate along the third axis relative to the first portion, and
wherein the third axis is parallel to the first axis and orthogonal to the second axis.

11. The adjustable implant of claim 10, wherein the first axis and the second axis form a first angle, and wherein the first axis and the third axis form a second angle different than the first angle.

12. An adjustable implant comprising:
a first portion configured to couple to a first bone segment;
a drive assembly disposed within the first portion and configured to rotate about a first axis, wherein the drive assembly comprises a driver configured to rotate about the first axis, and a drive shaft rotatably coupled to the driver;
a second portion configured to couple to a second bone segment and axially translate relative to the first portion along a second axis; and
a ratchet assembly disposed at least partially within the first and second portions,
wherein the ratchet assembly is configured to actuate axial translation relative to the first portion along the second axis in response to rotation of the drive assembly about the first axis, and to inhibit retraction of the second portion relative to the first portion along the second axis, and
wherein the driver comprises a rotatable permanent magnet configured to be rotated by an externally applied magnetic field.

13. The adjustable implant of claim 12, wherein each of the first and second portions comprises a flat plate, and wherein the first axis is orthogonal to the second axis.

14. The adjustable implant of claim 12, further comprising:
a gear assembly disposed within the first portion and configured to rotate in response to the rotation of the drive assembly, wherein the gear assembly comprises:
an input gear rotatably coupled to the drive shaft;
an output gear rotatably coupled to the input gear; and
an eccentric shaft rotatably coupled to the output gear,
wherein the eccentric shaft is configured to engage the ratchet assembly to actuate axial translation of the second portion along the second axis relative to the first portion in response to rotation of the drive assembly.

15. The adjustable implant of claim 14, wherein the ratchet assembly comprises:
a ratchet arm having a first end coupled to the second portion, and a second end rotatably coupled to the eccentric shaft, wherein the ratchet arm is configured to rotate within the first portion about the eccentric shaft in response to rotation of the drive assembly, thereby causing the second portion to axially translate along the second axis relative to the first portion;
a linear rack having a plurality of ratchet teeth disposed on the second portion; and
a pawl coupled to the first portion, wherein the pawl is configured to engage the plurality of ratchet teeth to inhibit retraction of the second portion along the second axis relative to the first portion.

16. The adjustable implant of claim 14, wherein the input gear comprises a beveled input gear, and the output gear comprises a beveled output gear configured to matingly engage the beveled input gear.

* * * * *